US00RE47084E

(19) United States
(12) Reissued Patent
Castan et al.

(10) Patent Number: US RE47,084 E
(45) Date of Reissued Patent: Oct. 16, 2018

(54) ORAL MEDICINAL PRODUCT WITH MODIFIED RELEASE OF AT LEAST ONE ACTIVE PRINCIPLE IN MULTIMICROCAPSULAR FORM

(71) Applicant: FLAMEL IRELAND LIMITED, Dublin (IE)

(72) Inventors: Catherine Castan, Soucieu en Jarest (FR); Florence Guimberteau, Montussan (FR); Remi Meyrueix, Lyons (FR); Gerard Soula, Meyzieu (FR)

(73) Assignee: FLAMEL IRELAND LIMITED, Dublin (IE)

(21) Appl. No.: 15/166,566

(22) Filed: May 27, 2016

Related U.S. Patent Documents

Reissue of:
(64) Patent No.: 8,734,850
Issued: May 27, 2014
Appl. No.: 10/996,780
Filed: Nov. 24, 2004

U.S. Applications:
(60) Provisional application No. 60/605,680, filed on Aug. 30, 2004, provisional application No. 60/524,991, filed on Nov. 25, 2003.

(51) Int. Cl.
*A61K 9/16* (2006.01)
*A61K 9/22* (2006.01)
(Continued)

(52) U.S. Cl.
CPC ..... *A61K 9/1635* (2013.01); *A61K 9/1641* (2013.01); *A61K 9/1658* (2013.01); *A61K 9/2077* (2013.01); *A61K 31/403* (2013.01)

(58) Field of Classification Search
CPC ..... A61K 9/1635
(Continued)

(56) References Cited

U.S. PATENT DOCUMENTS 4,434,153 A 2/1984 Urquhart et al.
4,720,387 A 1/1988 Sakamoto et al.
(Continued)

FOREIGN PATENT DOCUMENTS

EP 1 101 490 5/2001
EP 1 101 490 A1 5/2001
(Continued)

OTHER PUBLICATIONS

In the U.S. Patent and Trademark Office, Requirement for Restriction/Election in re: U.S. Appl. No. 10/996,780, dated Feb. 20, 2008, 11 pages.

(Continued)

*Primary Examiner* — Timothy J. Kugel

(57) ABSTRACT

The field of the invention is that of oral pharmaceutical medicinal products or compositions, more particularly of the type of those comprising one or more active principles.
The aim of the invention is to provide an improved oral medicinal product that can be administered in one or more daily doses, with modified release of active principle (in particular an active principle), for improving the prophylactic and therapeutic efficacy of such a medicinal product.
This aim is achieved by means of the multimicrocapsular oral pharmaceutical form according to the invention in which the release of the AP is controlled by means of a double mechanism of triggering the release: "time triggering" and "pH triggering". This medicinal product comprises microcapsules with modified release of active principle, each containing a core comprising the active principle and one or more swelling agents, and at least one coating making possible the modified release of the active principle.

74 Claims, 7 Drawing Sheets

(51) Int. Cl.
*A61K 31/403* (2006.01)
*A61K 9/20* (2006.01)

(58) Field of Classification Search
USPC ..... 424/490
See application file for complete search history.

(56) References Cited

U.S. PATENT DOCUMENTS

| | | | | |
|---|---|---|---|---|
| 4,753,802 | A | 6/1988 | Stephens et al. | |
| 4,844,905 | A | 7/1989 | Ichikawa et al. | |
| 5,007,790 | A * | 4/1991 | Shell | A61K 9/0065 424/451 |
| 5,326,570 | A | 7/1994 | Rudnic et al. | |
| 5,783,215 | A | 7/1998 | Arwidsson et al. | |
| 5,840,332 | A | 11/1998 | Lerner et al. | |
| 6,056,968 | A | 5/2000 | Gilbert et al. | |
| 6,110,494 | A | 8/2000 | Clancy et al. | |
| 6,352,721 | B1 | 3/2002 | Faour | |
| 6,491,949 | B2 | 12/2002 | Faour et al. | |
| 6,515,010 | B1 | 2/2003 | Franchini et al. | |
| 8,734,850 | B2 | 5/2014 | Castan et al. | |
| 2003/0035836 | A1 | 2/2003 | Shanghvi et al. | |
| 2004/0234601 | A1* | 11/2004 | Legrand et al. | 424/469 |
| 2005/0037077 | A1* | 2/2005 | Legrand et al. | A61K 9/5078 424/469 |

FOREIGN PATENT DOCUMENTS

| | | | |
|---|---|---|---|
| WO | 96/19201 | A1 | 6/1996 |
| WO | 99/24017 | A1 | 5/1999 |
| WO | 99/52526 | A1 | 10/1999 |
| WO | 01/05430 | A1 | 1/2001 |
| WO | 01/35958 | A1 | 5/2001 |
| WO | 02/065834 | A2 | 8/2002 |
| WO | 02/092078 | A1 | 11/2002 |
| WO | WO-03/030378 | | 4/2003 |
| WO | WO-03030378 | A2 | 4/2003 |
| WO | 03/097018 | A1 | 11/2003 |

OTHER PUBLICATIONS

In the U.S. Patent and Trademark Office, Office Action in re: U.S. Appl. No. 10/996,780, dated Dec. 12, 2008, 17 pages.
In the U.S. Patent and Trademark Office, Final Office Action in re: U.S. Appl. No. 10/996,780, dated Oct. 8, 2009, 18 pages.
In the U.S. Patent and Trademark Office, Office Action in re: U.S. Appl. No. 10/996,780, dated Sep. 26, 2011, 21 pages.
In the U.S. Patent and Trademark Office, Final Office Action in re: U.S. Appl. No. 10/996,780, dated May 31, 2012, 21 pages.
In the U.S. Patent and Trademark Office, Notice of Allowance in re: U.S. Appl. No. 10/996,780, dated Jan. 15, 2014, 12 pages.
Aoki et al., JP Application No. JPH10120571A, "Diltiazem hydrochloride sustained release preparation", filed May 12, 1998; 4 pgs. (English translation).
Exam report from related EP Application No. 04812185.9, dated Jan. 2, 2013; 5 pgs.
Exam report from related EP Application No. 04812185.9, dated Jan. 20, 2016; 4 pgs.
Examiner's Answer to Appeal Brief in related U.S. Appl. No. 10/997,836, dated Oct. 20, 2016; 20 pgs.
Office Action from related Japanese Application No. 2006-541444, dated Jan. 18, 2011; 3 pgs.
Office Action from related Japanese Application No. 2006-541724, dated Feb. 1, 2011; 3 pgs.
Office Action from related Japanese Application No. 2006-541724, dated Oct. 18, 2011; 3 pgs.
Office Action from related Japanese Application No. 2012-034491, dated Aug. 18, 2015; 3 pgs.
Office Action from related U.S. Appl. No. 10/997,836, dated Jan. 26, 2015; 14 pgs.
Office Action from related U.S. Appl. No. 10/997,836, dated Feb. 19, 2016; 20 pgs.
Office Action from related U.S. Appl. No. 10/997,836, dated Jun. 20, 2014; 16 pgs.
Office Action from related U.S. Appl. No. 10/997,836, dated Aug. 7, 2009; 12 pgs.
Office Action from related U.S. Appl. No. 10/997,836, dated Aug. 19, 2010; 20 pgs.
Office Action from related U.S. Appl. No. 10/997,836, dated Oct. 29, 2008; 12 pgs.
Office Action from related U.S. Appl. No. 10/997,836, dated Nov. 2, 2015; 19 pgs.
Office Action from related U.S. Appl. No. 11/137,261, dated Jan. 15, 2009; 23 pgs.
Office Action from related U.S. Appl. No. 11/137,261, dated Apr. 2, 2008; 17 pgs.
International Preliminary Report on Patentability from related International Application No. PCT/US2004/039614, dated May 29, 2006; 4 pgs.
International Preliminary Report on Patentability from related International Application No. PCT/US2004/039677, dated May 29, 2006; 5 pgs.
Davis et al., *The Design and Evolution of Controlled Release Systems for the Gastrointestinal Tract*, J. of Controlled Release, 2: 27-38 (1985).

* cited by examiner

ORAL MEDICINAL PRODUCT WITH MODIFIED RELEASE OF AT LEAST ONE ACTIVE PRINCIPLE IN MULTIMICROCAPSULAR FORM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

The present application claims priority to U.S. Provisional Patent Application No. 60/524,991, filed Nov. 25, 2003 and U.S. Provisional Patent Application No. 60/605,680, filed Aug. 30, 2004. The present application is related to U.S. Provisional Patent Application No. 10/996,780, filed Nov. 24, 2004; U.S. Provisional Patent Application No. 10/997,836, filed Nov. 24, 2004; and French Patent Application No. FR 0452748, filed Nov. 24, 2004.

FIELD OF THE INVENTION

The field of the present invention is that of microparticulate systems with delayed and controlled release of active principle(s), AP(s), intended for oral administration.

The APs envisaged in the present invention are in particular those which have an absorption that is essentially limited to the upper parts of the gastrointestinal tract, located upstream of the colon (of the ileocaecal junction), and which represent a large majority of pharmaceutical active principles. The active principles most specially targeted are active principles with "low solubility".

More precisely, the invention relates to a microparticulate pharmaceutical form with delayed and controlled release for which the controlled release phase is triggered in a definite manner by virtue of a double mechanism: "time-dependent" release triggered after a certain amount of time spent in the stomach, and "pH-dependent" release triggered by a change in pH when the particles enter the small intestine and which begins without any lag time. The microparticles of the present invention are microcapsules containing at least one active principle (AP), with the exclusion of carvedilol, of mean particle size less than 2000 microns, individually coated with a coating film allowing delayed and controlled release of the AP.

The invention also relates to the microcapsules with modified release of at least one active principle, taken as such.

In the present disclosure, the expression "active principle with low solubility" denotes any active principle, with the exclusion of carvedilol, having a solubility of less than or equal to approximately 50 g/l, preferably less than or equal to approximately 20 g/l, even more preferably less than or equal to approximately 5 g/l and, for example, less than or equal to 0.1 g/l.

In the present disclosure, the term "microcapsules" denotes microparticles of active principle that are film-coated with at least one coating allowing modified release of at least one active principle (in particular an active principle with low solubility).

In the present disclosure, the term "carvedilol" denotes carvedilol per se, one or more pharmaceutically acceptable salts of carvedilol, or one or more pharmaceutically acceptable esters of carvedilol or any mixture of these active agents.

In the present disclosure, the expression "modified release" denotes, without distinction, a prolonged release of the active principle(s), beginning as soon as the microcapsules are brought into contact with the dissolving medium and ranging from 0.5 h to 24 h, preferably from 1 to 10 h, or a release of the active principle(s) that begins only after a predetermined period of time (lag time) ranging, for example, from 0.5 to several hours, with a time for release of 50% of the active principle(s) which is typically several hours and which can range from 0.5 to 30 hours, for example.

In the present disclosure, the expression "immediate release" denotes a release of the active principle(s) that begins as soon as the pharmaceutical form is brought into contact with the dissolving medium (in vivo or in vitro) with a time for release of 80% of the active principle(s) which is less than or equal to 1 h and, for example, less than or equal to 20 min.

The systems with delayed and controlled release of active principle(s) are particularly useful when it is desirable, for chronobiological reasons, for the active principle(s) to be "bioabsorbed" at a precise time in the day in order to be in phase with the circadian cycle. It may, for example, be advantageous for the active principle(s) to be bioabsorbed very early in the morning in order to ensure therapeutic coverage when the patient wakes up, without however forcing him or her to wake up early. To do this, the pharmaceutical system ingested by the patient, for example in the evening after the meal, must allow a delayed release of the active principle(s).

Given that another rule imposed on the specialist in galenics is to guarantee that the medicinal product prescribed will be absorbed by the patient, it is essential, in the case of a delayed release form, to be entirely sure that the active principle will be released at a given instant so as to obtain the therapeutic effect. Now, it has to be noted that the delayed-release forms that existed until recent times could not definitely ensure release of the AP within a prescribed period, which can be vital for the patient in certain pathologies, such as, for example, that of cardiovascular diseases.

Another desired property for systems with delayed and controlled release of active principle(s) is an improvement in the plasma concentration profile obtained after administration. The targeted goal is to obtain a plasma profile that is maintained above the effective therapeutic concentration for as long as possible in order to maximize the duration of action of the active principle(s), and therefore its (their) therapeutic efficacy. This goal comes up against the residence time of the active principle(s) in the blood compartment, which is most commonly much less than a day. To achieve this aim, it would therefore be advisable to prolong the bioabsorption time of the active principle(s), AP(s), through a judicious adjustment of the release of the active principle(s) in front of its (their) bioabsorption window, in the upper parts of the gastrointestinal tract.

Various forms with modified release of active principle(s) have been developed, in order to attempt to solve the abovementioned problems of chronotherapy and of maintenance of a high plasma profile for as long as possible.

pH-dependent delayed-release forms are thus known, which are obtained by coating the active principle(s) by means of an enteric polymer layer, for example a layer of copolymer of methacrylic acid and of methacrylic acid methyl ester: EUDRAGIT® L. This type of enteric coating is known to exhibit a reduced permeability under the acidic pH conditions of the stomach and to dissolve when the pH goes back up to a value close to that which reigns in the small intestine, thus releasing the active principle(s). However, the intraindividual and interindividual variability of the gastric pH conditions and of the gastric emptying time do not make it possible to definitely ensure release of the active principle(s) after a given period of time.

Systems with delayed release that is purely dependent on the time after ingestion ("time-dependent") are, moreover, known, i.e. systems for which the release of the active principle(s) is initiated after a given period of time spent in the gastrointestinal tract, which are not satisfactory either. In fact, due to the intraindividual and interindividual variability in gastric residence time, the release of the active principle(s) can occur after said active principle(s) has(have) passed in front of its(their) absorption window, which is located, for most active principles, in the upper parts of the gastrointestinal tract. The bioabsorption can thus be very poor or even zero.

However, it needed the advent of the multimicroparticulate pharmaceutical system as disclosed in PCT patent application WO-A-03/030878 to obtain very significant progress, in particular with regard to the abovementioned problems of chronotherapy and of maintenance of a high plasma profile for as long as possible. This system with delayed, controlled and definite release of the active principle(s) is characterized by a double mechanism for triggering the release of the active principle(s): "time-dependent" release triggered after a controlled period of time in the stomach, without change in pH, and "pH-dependent" release triggered by a rise in pH when the pharmaceutical form enters the intestine. These two factors triggering the release of the active principle(s) are placed in series and confer on the pharmaceutical system a great safety of use. The release of the active principle(s) is thus guaranteed after a preset lag time, even if the variation in pH has not intervened as a trigger, i.e. even if the pharmaceutical form has not passed from the stomach into the intestine. These microcapsules with a diameter between 200 and 600 microns are characterized by a coating film based on a hydrophilic polymer A of the EUDRAGIT® L type combined with a hydrophobic compound B, such as a vegetable wax (LUBRITAB®), with a melting temperature of between 40 and 90° C.; the B/A ratio=0.2-1.5. The in vitro dissolving behavior of these microcapsules is such that, at constant pH 1.4, a lag phase of between 1 and 5 hours is observed, followed by an active principle release phase, and such that the change from pH 1.4 to pH 6.8 results in release of the active principle without any lag time in vitro.

The multimicroparticulate pharmaceutical system according to PCT patent application WO-A-03/030878 also makes it possible to adjust the lag time preceding the release of the AP in the stomach by taking into consideration the physiological conditions of the gastrointestinal tract in humans. This advantageous modality is thus a means of minimizing the interindividual variability of the absorption of the AP. In fact, according to the well known results of Davis et al., J. of Controlled Release, 2, 27-38 (1985), the residence time of a preparation in the stomach is very variable, of the order of 0.5 to 10 hours. Now, precisely, the abovementioned system makes it possible to release the active principle in the stomach after a given lag time, which is constant and within this 0.5-10 hour range, in such a way that, from one individual to another, or even from one day to another for the same individual, the action time for the medicinal product is the same.

In fact, the microparticulate oral pharmaceutical form with delayed and controlled release of AP, according to WO-A-03/03878, has simultaneously the following properties:

- the release of the AP can be initiated in two ways:
  - by time-dependent release when the amount of time spent by the particles in the stomach exceeds a period of 5 hours;
  - by pH-dependent release, which begins without any lag time when the system passes into the intestine and when the pH increases. These two factors triggering the release of AP placed in series guarantee release of the AP after a preset lag time, even if the variation in pH has not intervened as a trigger;
- it consists of a plurality of small microcapsules of coated AP;
- the mass fraction of coating excipients is limited.

It should be noted that the problem of maintaining a high plasma profile for as long as possible can be solved, in accordance with the invention according to WO-A-03/03878, by using a mixture of microcapsules with different profiles of delayed and controlled release. This makes it possible to produce release profiles exhibiting several waves of release or providing, by means of appropriate regulation of the various fractions, a constant level of concentration of the active principle(s) in the plasma.

TECHNICAL PROBLEM

It nevertheless remains that this microparticulate oral pharmaceutical form with delayed and controlled release of active principle(s), according to WO-A-03/03878, can be further improved.

In fact, it is known that, in order to be released, a microencapsulated active principle must first of all be reached by the fluids of the gastrointestinal tract, which must, in order to do this, cross the coating film of the microcapsules. The microencapsulated active principle can then dissolve in these fluids. The solution of active principle thus obtained can then diffuse out through the coating film(s) of the microcapsules. Thus, in order to obtain a lag time of between 0.5 and 7 h, for example of 2-3 h, it is important for the coating film of the microcapsules to have a sufficient thickness (in μm) and/or to represent a sufficient degree of coating DC (as % by weight) in order for the time of entry of a liquid such as water or a gastrointestinal tract fluid into the microcapsule allows delayed release of the active principle. This floor value may, for example, correspond to a DC of 10-40%, for example.

However, when the thickness of the film-coating is sufficient to result in a lag time, it has been possible to observe that, in the case of active principles with low solubility, the "time-dependent" release, just like the "pH-dependent" release, of the active principle are still as effective, but become slower, which can harm the bioavailability. For example, at least 80% by weight of the active principle is not released after, for example, 16 h at pH=7.0, in an in vitro dissolution test carried out according to the indications of the European Pharmacopoeia, 4th edition, entitled: "Dissolution test for solid oral forms": type II dissolutest carried out under SINK conditions, maintained at 37° C. and agitated at 100 rpm.

There exists therefore, at this time, a need for a multimicrocapsular oral medicinal product or pharmaceutical composition, with modified release of active principle(s), which is of the type of those disclosed in WO-A-03/030878 and which improves them, by making it possible in particular to obtain, for active principles with low solubility, release of the active principle according to a double mechanism of "time-dependent" and "pH-dependent" triggering, with faster release times which make it possible to optimize the bioabsorption of the active principle(s), whatever the mechanism for triggering this release.

OBJECTIVES

One of the essential objectives of the invention is to provide an oral medicinal product that is improved with respect to that described in WO-A-03/03878, precisely a multimicrocapsular oral medicinal product with modified release of active principle(s), in particular of active principle(s) with low solubility or solubilities, which guarantees correct functioning of the double mechanism of "time-dependent" and "pH-dependent" triggering of the release of the active principle, in particular for active principles with low solubilities.

Another essential objective of the invention is to provide a multimicrocapsular oral medicinal product with modified release of active principle(s), which makes it possible to judiciously adjust the release kinetics of the active principle all along its window of absorption in the gastrointestinal tract in order for the plasma concentration profile to be maintained above the effective therapeutic concentration for as long as possible, and in particular for a period of time greater than that of the immediate-release form.

Another essential objective of the invention is to provide a multimicrocapsular oral medicinal product with modified release of active principle(s), which proposes a solution suitable for the problem of chronotherapy and for the difficulties of adherence pertaining thereto.

Another essential objective of the invention is to provide a multimicrocapsular oral medicinal product with modified release of active principle(s), which makes it possible to readily combine at least two active principles in the same pharmaceutical form.

Another essential objective of the invention is to provide a multimicrocapsular oral medicinal product with modified release of active principle(s), which, unlike the compact monolithic forms, provides a decreased interindividual variability.

Another essential objective of the invention is to provide a multimicrocapsular oral medicinal product with modified release of active principle(s), which allows an increase in the gastrointestinal transit time and absorption of the active principle in the upper parts of the gastrointestinal tract.

Another essential objective of the invention is to provide a multimicrocapsular oral medicinal product with modified release of active principle(s), this medicinal product being able to exist in a presentation form that can be administered once a day, which would represent significant progress, in particular in terms of the patient adhering to the treatment.

Another essential objective of the invention is to provide a multimicrocapsular oral medicinal product with modified release of active principle(s), which may be produced according to a sound industrial process.

Another essential objective of the invention is to provide a multimicrocapsular oral medicinal product with modified release of active principle(s), which is easy to prepare, for example by depositing a coating by spraying onto microparticles containing active principle with low solubility.

Another essential objective of the invention is to provide a multimicrocapsular oral medicinal product with modified release of active principle(s), capable of exhibiting high contents of active principle(s), for example up to 60% by weight of the microcapsules.

Another essential objective of the invention is to provide an oral medicinal product with modified release of active principle(s), containing a plurality of microcapsules and having a dose-independent active principle release profile, in vitro.

Another essential objective of the invention is to provide a multimicrocapsular oral medicinal product with modified release of active principle(s), in which the microcapsules are nonenteric, i.e. they do not release the active principle only when the pH changes from 1.4 to 7.0 (gastric pH=>intestinal pH).

Another essential objective of the invention is to provide a multimicrocapsular oral medicinal product with modified release of active principle(s), which makes it possible to obtain a plasma concentration (C24h) of active principle(s) 24 h after administration per os that is as high as possible.

Another essential objective of the invention is to provide microcapsules with modified release of active principles that can be used in particular for preparing a medicinal product as defined by the specifications stated in the above objectives.

BRIEF DISCLOSURE OF THE INVENTION

These objectives, among others, are achieved by means of the invention which relates, firstly, to an oral medicinal product comprising a plurality of microcapsules with modified release of active principle(s), at least some of said microcapsules individually consisting of a microparticle comprising at least one active principle—in particular at least one active principle with low solubility—(with the exclusion of carvedilol) coated with at least one coating for modified release of the active principle(s), said release being controlled by means of two distinct triggering mechanisms, one being based on a variation in pH and the other allowing the release of the active principle(s) after a predetermined period of residence in the stomach, said coating also conferring on the microcapsules an in vitro dissolution behavior such that:

at constant pH 1.4, the dissolution profile comprises a lag phase of less than or equal to 7 hours, preferably less than or equal to 5 hours, and even more preferably of between 1 and 5 hours;

the change from pH 1.4 to pH 7.0 results in a release phase that begins without any lag time;

this medicinal product being characterized in that at least some of said microcapsules comprise at least one swelling agent, and in that the fraction by weight of the active principle(s) released during the lag phase is less than or equal to 15% by weight per hour, preferably less than or equal to 10% by weight per hour, and even more preferably less than or equal to 5% by weight per hour.

The in vitro dissolution behavior is determined according to the indications of the European Pharmacopoeia, 4th edition, entitled: "Dissolution test for solid oral forms": type II dissolutest performed under SINK conditions, maintained at 37° C. and agitated at 100 rpm.

The medicinal product according to the invention overcomes the abovementioned technical problem, namely the release of active principle(s), AP(s), with low solubility according to a double mechanism of "time-dependent" and "pH-dependent" triggering, by accelerating the release of the active principle, in particular compared to the release times obtained by means of the invention according to WO-A-03/03878. In doing this, the medicinal product according to the invention ultimately improves the prophylactic and therapeutic efficacy of such active principles with low solubility.

However, the medicinal product according to the invention is also interesting in that it provides in particular the following advantages:

- the possibility of simple combined use of at least two active principle(s);
- decreased interindividual variability;
- an increase in the gastrointestinal transit time and absorption of the active principle in the upper parts of the gastrointestinal tract;
- proportionality between the dose and the pharmacokinetic profile;
- ease of ingestion by the patient and the possibility of administration, for example, once a day, which is an indication of the treatment being adhered to by the patient and therefore of the effectiveness being guaranteed;
- reproducibility of the kinetics of release, from one industrial batch to another; therefore possible industrial development, without this harming the therapeutic performance of the active principle(s) encapsulated (for example active principles with low solubility);
- easy and economical preparation, for example by depositing a coating by spraying onto microparticles containing active principle with low solubility;
- possibility of having high concentrations of active principle(s), for example up to 60% by weight of the microcapsules;
- plurality of microcapsules and having a dose-independent active principle release profile, in vitro;
- nonenteric microcapsules, i.e. that do not release the active principle only when the pH changes from 1.4 to 7.0 (gastric pH=>intestinal pH);
- plasma concentration of active principle(s) 24 h after administration per os close to or greater than that which would be obtained with an immediate-release form taken in several doses.

DETAILED DISCLOSURE OF THE INVENTION

In accordance with the invention, the swelling agent comprises at least one hydrophilic pharmaceutically acceptable compound exhibiting a degree of swelling in water at 25° C. of greater than or equal to 10% by weight, preferably greater than or equal to 15% by weight, and even more preferably greater than or equal to 20%.

According to a notable characteristic of the invention, the swelling agent is chosen from those that allow the microcapsules to release at least 50% by weight of the active principle after 16 h at pH=1.4 and after a lag phase of less than or equal to 7 hours, preferably less than or equal to 5 hours, and even more preferably of between 1 and 5 hours, in an in vitro dissolution test carried out according to the indications of the European Pharmacopoeia, 4th edition, entitled: "Dissolution Test for Solid Oral Forms": type II dissolutest performed under SINK conditions, maintained at 37° C. and agitated at 100 rpm.

In accordance with the invention, it is possible to adjust the rate of release at pH=1.4 of the active principle(s) out of the microcapsules by judiciously choosing the concentration (Cd) of swelling agent.

When the swelling agent is in microparticulate form, the size (Sd) of the particles of swelling agent is advantageously chosen within the ranges of mean diameter in μm of between 5 and 200 μm, and preferably between 10 and 50 μm.

The concentration (Cd) of swelling agent is chosen within the following ranges of % by weight relative to the total mass of the microcapsules:

$3 \leq Cd \leq 40$, preferably $4 \leq Cd \leq 30$, and even more preferably $5 \leq Cd \leq 25$.

According to a preferred embodiment of the invention, the swelling agent is chosen from the group of products below:

- crosslinked polyvinylpyrrolidones (e.g. polyplasdone or crospovidone),
- crosslinked carboxyalkylcelluloses: crosslinked carboxymethylcelluloses (e.g. crosslinked sodium croscarmellose),
- and also high molar mass hydrophilic polymers (greater than or equal to 100 000 D), such as:
  - polyvinylpyrrolidones,
  - polyalkylene oxides (e.g. polyethylene oxide or polypropylene oxide),
  - (hydroxy)(alkyl)celluloses (e.g. hydroxypropylcellulose, hydroxypropylmethylcellulose),
  - carboxyalkylcelluloses (e.g. carboxymethylcellulose),
  - celluloses (powder or microcrystalline),
  - modified starches (for example modified with sodium glycolate),
  - natural starches (for example cornstarch, wheat starch or potato starch),
  - sodium alginate,
  - polacrilin potassium,
  - and mixtures thereof.

Even more preferably, the swelling agent is chosen from the subgroup of products below:

- crosslinked polyvinylpyrrolidones (e.g. polyplasdone or crospovidone), and
- crosslinked carboxyalkylcelluloses: crosslinked carboxymethylcelluloses (e.g. crosslinked sodium croscarmellose).

In order to overcome the eventuality where active principles (for example with low solubility) are poorly wetted by water and therefore have a tendency to agglomerate, it is proposed, according to an advantageous variant of the invention, to operate such that the medicinal product comprises at least one wetting agent, preferably chosen from the group of products below:

- anionic surfactants, preferably from the subgroup of alkali metal or alkaline-earth metal salts of fatty acids, stearic acid and/or oleic acid being preferred,
- and/or nonionic surfactants, preferably from the subgroup below:
  - polyoxyethylenated oils, preferably polyoxyethylenated hydrogenated castor oil,
  - polyoxyethylene-polyoxypropylene copolymers,
  - polyoxyethylenated esters of sorbitan,
  - polyoxyethylenated derivatives of castor oil,
  - stearates, preferably calcium stearate, magnesium stearate, aluminum stearate or zinc stearate,
  - stearylfumarates, preferably sodium stearylfumarate,
  - glyceryl behenate,
  - and mixtures thereof.

Advantageously, the medicinal product according to the invention comprises microcapsules of active principle(s) capable of releasing at least 80% by weight of the active principle(s), after 12 h at pH=7.0, in an in vitro dissolution test carried out according to the indications of the European Pharmacopoeia, 4th edition, entitled: "Dissolution Test for Solid Oral Forms": type II dissolutest performed under SINK conditions, maintained at 37° C. and agitated at 100 rpm.

The medicinal product according to the invention is multimicrocapsular, i.e. it comprises, inter alia, microcapsules consisting of microparticles of coated or film-coated active principle. These microparticles of active principle may, for example, be microparticles of the (pure) crude active principle in pulverulent form, matrix granules of active principle with various other ingredients, or alternatively neutral microspheres, for example made of cellulose or of sugar, coated with at least one layer comprising active principle.

The microcapsules of active principle with modified release are comparable to microunits containing at least one active principle and forming at least some of the elements constituting the medicinal product according to the invention.

Each microcapsule can comprise one or more active principles that are identical to or different from one another.

The medicinal product according to the invention can comprise microunits of active principle other than microcapsules. These may be, for example, microparticles with immediate release of active principle(s). The latter may be, for example, noncoated microparticles of active principle(s) that are of the same type as those used in the preparation of the microcapsules according to the invention.

Each microparticle may comprise one or more active principles that are identical to or different from one another.

In addition, all the microunits (microparticles and/or microcapsules) constituting the medicinal product according to the invention may be made up of various populations of microunits, these populations differing from one another at least through the nature of the active principle(s) contained in these microunits and/or through the composition of the coating.

As regards the structure of the microcapsules used in the medicinal product according to the invention, two preferred embodiments of the structure of the microcapsules are given in detail hereinafter, without any implied limitation.

According to a first embodiment, at least some of the microcapsules with modified release of active principle(s) each comprise:

- a microparticle of active principle(s) coated with
- at least one coating for modified release of the active principle(s).

Preferably, the microparticle of active principle(s) is a granule comprising the active principle(s) and one or more pharmaceutically acceptable excipients.

Advantageously, the swelling agent(s) is (are) contained in the microparticles (e.g. granule).

As regards the wetting agent(s), it (they) is (are) preferably contained in the microparticle (e.g. granule) and/or in the coating for modified release of the active principle(s).

According to a second embodiment, at least some of the microcapsules with modified release of active principle(s) each comprise:

- a neutral core,
- at least one active layer comprising the active principle(s) and coating the neutral core, and
- at least one coating for modified release of the active principle(s).

According to a first possibility, the neutral core contains sucrose and/or dextrose and/or lactose.

According to a second possibility, the neutral core is a cellulose microsphere.

Advantageously, the neutral core has a mean diameter of between 1 and 800 μm, and preferably of between 20 and 500 μm.

The active layer may optionally comprise, besides the active principle(s), one or more pharmaceutically acceptable excipients.

Advantageously, the swelling agent(s) is (are) contained in the active layer.

For example, this active layer comprises the active principle, at least one swelling agent, at least one binder and at least one surfactant.

As regards the wetting agent(s), it (they) is (are) preferably contained in the active layer.

With regard, now, to the composition of the coating of the microcapsules with modified release of active principle(s), the present invention also consisted in selecting microcapsules having the following specificities:

- the coating making possible modified release of the active principle(s) comprises a composite material comprising:
  - at least one hydrophilic polymer A carrying groups that are ionized at neutral pH,
  - at least one hydrophobic compound B;
  - representing a mass fraction (% weight relative to the total mass of the microcapsules)≤40; and
- their mean diameter is less than 2000 μm, and preferably between 50 and 800 μm, and even more preferably between 100 and 600 μm.

According to another advantageous characteristic, the composite material AB for the coating making possible modified release of the active principle with low solubility is such that:

- the B/A weight ratio is between 0.2 and 1.5, preferably between 0.5 and 1.0,
- and the hydrophobic compound B is selected from products that are crystalline in the solid state and that have a melting point $T_{mB} \geq 40°$ C., preferably $T_{mB} \geq 50°$ C., and even more preferably 40° C.$\leq T_{mB} \leq 90°$ C.

According to an embodiment of predilection, the hydrophilic polymer A is chosen from:

- A.a copolymers of (meth)acrylic acid and of (meth) acrylic acid alkyl ester, and mixtures thereof;
- A.b cellulose derivatives, preferably cellulose acetates, cellulose phthalates, cellulose succinates and mixtures thereof, and even more preferably hydroxypropylmethylcellulose phthalates, hydroxypropylmethylcellulose acetates, hydroxypropylmethylcellulose succinates and mixtures thereof;
- and mixtures thereof.

The polymers A that are even more preferred are copolymers of (meth)acrylic acid and of (meth)acrylic acid alkyl (e.g. $C_1$-$C_6$ alkyl) esters. These copolymers are, for example, of the type of those sold by the company Röhm Pharma Polymers under the registered trade marks EUDRAGIT®, series L and S (such as, for example, EUDRAGIT® L100, S100, L30 D-55 and L100-55). These copolymers are anionic enteric copolymers that are soluble in aqueous medium at pHs above those encountered in the stomach.

Still according to the embodiment of predilection, the compound B is chosen from the group of products below:

- B.a vegetable waxes taken on their own or as mixtures with one another;
- B.b hydrogenated vegetable oils taken on their own or as mixtures with one another;
- B.c mono- and/or di- and/or triesters of glycerol and of at least one fatty acid;

B.d mixtures of monoesters, of diesters and of triesters of glycerol and of at least one fatty acid;

B.e and mixtures thereof.

Even more preferably, the compound B is chosen from the group of following products: hydrogenated cottonseed oil, hydrogenated soybean seed oil, hydrogenated palm oil, glyceryl behenate, hydrogenated castor oil, tristearin, tripalmitin, trimyristin, yellow wax, hard fat or fat that is useful as suppository bases, anhydrous dairy fats, lanolin, glyceryl palmitostearate, glyceryl stearate, lauryl macrogolglycerides, cetyl alcohol, polyglyceryl diisostearate, diethylene glycol monostearate, ethylene glycol monostearate, omega 3 and any mixture thereof, preferably from the subgroup of following products: hydrogenated cottonseed oil, hydrogenated soybean seed oil, hydrogenated palm oil, glyceryl behenate, hydrogenated castor oil, tristearin, tripalmitin, trimyristin and any mixture thereof.

In practice, and without this being limiting, it is preferable for the compound B to be chosen:

from the group of products sold under the following trade marks: Dynasan®, Cutina®, Hydrobase®, Dub®, Castorwax®, Croduret®, Compritol®, Sterotex®, Lubritab®, Apifil®, Akofine®, Softtisan®, Hydrocote®, Livopol®, Super Hartolan®, MGLA®, Corona®, Protalan®, Akosoft®, Akosol®, Cremao®, Massupol®, Novata®, Suppocire®, Wecobee®, Witepsol®, Lanolin®, Incromega®, Estaram®, Suppoweiss®, Gelucire®, Precirol®, Emulcire®, Plurol diisostéarique®, Geleol®, Hydrin® and Monthyle®, and mixtures thereof;

and also from the group of additives for which the codes are as follows: E 901, E 907, E 903 and mixtures thereof;

and, preferably, from the group of products sold under the following trade marks: Dynasan® P60, Dynasan® 114, Dynasan® 116, Dynasan® 118, Cutina® HR, Hydrobase® 66-68, Dub® HPH, Compritol® 888, Sterotex® NF, Sterotex® K, Lubritab® and mixtures thereof.

According to another advantageous characteristic of the invention, the coating for modified release of the active principle with low solubility is free of talc.

According to another notable characteristic resulting from the preparation of the microcapsules, the active principle is deposited onto the core by means of techniques known to those skilled in the art, for example the technique of "spray coating" in a fluidized air bed, wet granulation, compacting, extrusion-spheronization, etc.

Advantageously, the coating of the microcapsules may comprise, besides the essential constituents A and B, other conventional ingredients known to those skilled in the art, such as in particular:

colorants, plasticizers, for instance dibutyl sebacate, hydrophilic compounds, for instance cellulose and its derivatives or polyvinylpyrrolidone and its derivatives, and mixtures thereof.

Without it being limiting and according to an even more preferred embodiment, the coating of the microcapsules with modified release of active principle comprises a single composite AB coating film.

In quantitative terms, the coating monolayer can represent, for example, at most 40%, preferably at most 30%, by weight of the microcapsules. Such a limited amount of coating makes it possible to produce pharmaceutical units each containing a high dose of active principle, without exceeding a size that is totally unacceptable with regard to swallowing. This can only improve adherence to and therefore the success of the treatment.

The mechanism of triggering the release of the active principle with low solubility without variation in pH, after a predetermined period of residence in the stomach, results in particular from the control of the rate of hydration of the microcapsules and/or of the dissolution of one or more components of the microcapsules. For example, and without wishing to be limiting, the hydration of the microcapsule can be controlled:

by the presence, in the microcapsules, of hydrophilic products which make it possible to adjust the osmotic pressure or to cause swelling of the microcapsules;

or by regulation of the water-permeability of the coating film;

or by creation of a microporosity in the coating film;

or even by hydration or dissolution of a compound of the coating film.

One of the determining advantages of the multimicrocapsular pharmaceutical system with delayed and controlled release of active principle(s)—for example of principle(s) with low solubility—according to the invention, is to involve, in vivo, two factors triggering the release of the active principle(s)—for example of the principle(s) with low solubility—in the gastrointestinal tract, namely:

the amount of time spent in the stomach: "time-triggered" release, the variation in pH: "pH-triggered" release.

These two factors triggering the release of the active principle(s)—for example of principle(s) with low solubility—are in series, such that they confer on the pharmaceutical system a great safety of use. Release of the active principle(s)—for example of the principle(s) with low solubility—is thus guaranteed after a preset lag time, even if the variation in pH has not intervened as a trigger. The problems of interindividual variability are thus overcome. The therapeutic efficacy of the medicinal product comprising such a pharmaceutical system is ensured, observing a predetermined chronobiology that is suitable for the targeted therapeutic performance level.

In addition, for any active principle (e.g. with low solubility) for which the window of absorption is limited to the upper parts of the gastrointestinal tract, it is particularly advantageous for the form with delayed and then with prolonged and controlled release to be made up of a plurality of microcapsules. In fact, for such a pharmaceutical form, the dose of active principle (e.g. with low solubility) to be administered is divided up between a large number of microcapsules (typically 5,000-50,000) and, as a result, exhibits the following intrinsic advantages:

The amount of time spent by the microcapsules in the upper parts of the gastrointestinal tract can be prolonged, which ensures an increase in the amount of time spent by the active principle with low solubility in passing in front of the windows of absorption, and thus maximizes the bioavailability of the active principle with low solubility.

The use of a mixture of microcapsules having different delayed and controlled release profiles makes it possible to produce release profiles exhibiting several waves of release or providing, by means of suitable regulation of the various fractions, a constant level of concentration in the plasma of the active principle with low solubility.

The variability in gastric emptying is less, since the emptying which here takes place over a large number of particles is statistically more reproducible.

A situation where the tissues come into contact with a high dose of active principle with low solubility, "dose dumping", is prevented. Each microcapsule in fact contains only a very low dose of active principle with low solubility. The risk of deterioration of the tissues due to a local overconcentration of aggressive active principle with low solubility is thus avoided.

It is possible to provide these microcapsules in the form of a sachet, a gelatin capsule or a tablet. When the dose of active principle with low solubility is high (500 mg or more), the monolithic forms are too large to be easily swallowed. It is then particularly advantageous to have a microparticulate form which provides delayed and controlled release of the active principle (in particular with low solubility) and that those skilled in the art can formulate as tablets that can disintegrate or as sachets.

The multimicrocapsular pharmaceutical system according to the invention makes it possible to safely provide a delayed and controlled release of the active principle with low solubility in the gastrointestinal tract, by virtue of two triggers, and to thus avoid the interindividual and intraindividual variability of the gastric emptying conditions, while at the same time being economically viable and easy to ingest (optimized adherence to the treatment).

Another subject of the invention concerns an oral medicinal product comprising a plurality of microcapsules with modified release of active principle(s), at least some of said microcapsules individually consisting of a microparticle comprising at least one active principle—in particular at least one active principle with low solubility—(with the exclusion of carvedilol), coated with at least one coating for modified release of the active principle(s), said release being controlled by means of two distinct triggering mechanisms, one based on a variation in pH and the other allowing release of the active principle(s) after a predetermined residence time in the stomach, said coating:

also conferring on the microcapsules an in vitro dissolution behavior (determined according to the indications of the European Pharmacopoeia, 4th edition, entitled: "Dissolution Test for Solid Oral Forms": type II dissolutest performed under SINK conditions, maintained at 37° C. and agitated at 100 rpm) such that:

at constant pH 1.4, the dissolution profile comprises a lag phase of less than or equal to 7 hours, preferably less than or equal to 5 hours, and even more preferably of between 1 and 5 hours;

at least 50% by weight of the active principle(s) is released after 16 h at pH 1.4;

the change from pH 1.4 to pH 7.0 results in a release phase that begins without any lag time;

and comprising a composite material comprising at least one hydrophilic polymer A carrying groups that are ionized at neutral pH and at least one hydrophobic compound B;

this medicinal product being characterized in that at least some of said microcapsules comprise at least one release helper capable of increasing the permeability of the coating for modified release of the active principle(s), and in that the fraction by weight of the active principle(s) released during the lag phase is less than or equal to 15% by weight per hour, preferably less than or equal to 10% by weight per hour, and even more preferably less than or equal to 5% by weight per hour.

It in fact appeared to be useful in accordance with the invention to provide for, in the microcapsules, one or more helpers capable of increasing the permeability of the coating so as to reduce the release time, in particular for active principles with low solubility.

Advantageously, the release helper consists of at least one swelling agent, as defined above.

The medicinal product according to this other subject of the invention is also notable in that the coating of the microcapsules included in this medicinal product confers on said microcapsules an in vitro dissolution behavior (determined according to the indications of the European Pharmacopoeia, 4th edition, entitled: "Dissolution Test for Solid Oral Forms": type II dissolutest performed under SINK conditions, maintained at 37° C. and agitated at 100 rpm), such that at least 50% by weight of the active principle(s) is released after 16 h at pH 1.4.

The fact that the medicinal product according to the invention consists of a plurality of microunits makes it possible to obtain another essential characteristic of the invention, according to which the medicinal product comprises a mixture of various populations of microunits containing active principle(s) (with the exclusion of carvedilol), these populations differing from one another through their respective in vitro dissolution profiles, for at least one pH value of between 1.4 and 7.4.

This essential characteristic makes it possible to obtain an increase in the bioabsorption time for the active principle(s) and therefore in the time during which the plasma concentration is greater than the minimum effective concentration of this active principle.

In fact, the mixture of various populations of microunits (e.g. microcapsules with modified release of active principle and, optionally, microparticles with immediate release of active principle) results in a preferential release of the active principle(s) at different sites in the gastrointestinal tract, over the entire extent of the window of bioabsorption of the active principle(s) in the gastrointestinal tract.

According to an advantageous embodiment of this characteristic of mixture of various populations of microunits, the medicinal product according to the invention is characterized in that the microunits are microcapsules with modified release of active principle(s) and, optionally, microunits with immediate release of active principle(s).

Advantageously, the populations of microcapsules with modified release of active principle(s) differ through their respective triggering pHs.

The populations of microcapsules with modified release of active principle(s) can not only differ through their respective triggering pHs, but also through their respective triggering times, or even through their respective triggering pHs and times.

According to a preferred embodiment of this property of mixing populations, the medicinal product comprises:

i. at least one population of microunits containing active principle with immediate release;

ii. at least one population P1 of microcapsules with modified release of active principle(s); and iii. at least one population P2 of microcapsules with modified release of active principle(s);

and, moreover, the respective triggering pHs of P1 and of P2 differ by at least 0.5 of a pH unit, preferably by at least 0.8 of a pH unit, and even more preferably by at least 0.9 of a pH unit.

According to a preferred arrangement relating to the triggering pHs that differentiate the various populations of microcapsules with modified release of active principle(s), said respective triggering of pHs are between 5 and 7.

According to another variant of the preferred embodiment of this property of mixing populations, the medicinal product comprises:

i. at least one population of microunits containing active principle(s) with immediate release;

ii. at least one population P1' of microunits containing active principle(s), made up of microcapsules with modified release of the active principle(s), for which the triggering pH is equal to 5.5; and iii. at least one population P2' of microunits containing active principle(s), made up of microcapsules with modified release of the active principle(s), for which the triggering pH is equal to 6.0 or 6.5.

The release profile (measured in an in vitro release test as defined above) for the microcapsules with modified release used in the abovementioned mixtures of various populations of microunits (for example P1 & P2 or P1' & P2') may be, for example, as indicated below:

less than 20% of the active principle(s) is released after 2 hours at pH=1.4;

at least 50% of the active principle(s) is released after 16 hours at pH=1.4.

When the medicinal product according to the invention comprises at least one population of microunits containing active principle(s) with immediate release, this population can advantageously be defined by means of its behavior in an in vitro dissolution test, said behavior being such that at least 80% of the active principle(s) is released in 1 hour at a pH of between 1.4 and 7.4.

According to an advantageous property of the invention, the proportion of active principle(s) with low solubility in the microunits containing active principle(s) (expressed as % by weight on a dry basis relative to the total mass of the microunits) is between 5 and 80, preferably between 10 and 70, and even more preferably between 15 and 60.

Preferably, the microunits containing active principle(s) with immediate release are noncoated microparticles.

Without wishing to be limiting, it should nevertheless be underlined that the medicinal product according to the invention is particularly interesting in that it can be provided in the form of a single daily oral dose comprising from 5,000 to 50,000 microunits containing active principle(s), or from 5,000 to 50,000 microcapsules with modified release of active principle(s).

This plurality of microcapsules illustrated by the numerical examples mentioned above constitutes a pharmaceutical form that is perfectly well tolerated by the mammalian organism.

These microcapsules are all the more interesting since the production thereof is carried out simply and economically according to techniques well known to those skilled in the art, for example the technique of spray coating in a fluidized air bed, wet granulation, compacting, extrusion-spheronization, etc.

For further details regarding the preparation of these microcapsules, in particular in their embodiment with a neutral core coated with at least one active layer comprising active principle(s) and with at least one outer coating making possible modified release of the active principle(s), reference will be made to the content of PCT application WO-A-FR03/030878, whose content is integrated into the present disclosure by reference.

The medicinal product in the multimicroparticulate oral pharmaceutical forms according to the invention can be a tablet, advantageously an orally dispersible tablet, a powder, a liquid suspension or a gelatin capsule containing microcapsules.

In other words, this medicinal product can be provided in the form of a sachet of microcapsule powder, a liquid suspension of microcapsules, a tablet obtained from microcapsules, or a gelatin capsule containing microcapsules.

These tablets, gelatin capsules, powders and suspensions may consist of mixtures of the various populations of microunits, and in particular of microcapsules of active principle(s) according to the invention, preferably combining therewith microunits or microparticles with immediate release of active principle with low solubility (for example granules).

Moreover, the invention is directed towards the use of the microcapsules with modified release of the active principle(s) as defined above, and, optionally, of the microunits containing active principle(s) with immediate release, for preparing pharmaceutical or dietetic, microparticulate oral pharmaceutical forms, preferably in the form of tablets, which are advantageously orally dispersible, powders or gelatin capsules.

In addition, the invention relates to the microcapsules as defined above, taken as such.

Preferably, the active principle(s) may be chosen from at least one of the following major varieties of active substances, e.g.: antiulcer agents, antidiabetic agents, anticoagulants, antithrombics, blood lipid-lowering agents, antiarythmics, vasodilators, anti-angina agents, antihypertensives, vasoprotective agents, fertility promoters, inducers and inhibitors of uterine labor, contraceptives, antibiotics, antifungal agents, antiviral agents, anticancer agents, anti-inflammatories, analgesics, antiepileptics, antiparkinsonian agents, neuroleptics, hypnotics, anxiolytics, psychostimulants, antimigraine agents, antidepressants, antitussives, antihistamines or anti-allergic agents, agents for combating congestive heart failure, angina pectoris, left ventricular hypertrophy, cardiac arythmias, myocardial infarctions, reflex tachycardia, ischaemic heart disease, atheromatosis, hypertension related to diabetes mellitus, portal hypertension, dizziness, bradycardia, arterial hypotension, hydrosodic retention, acute kidney failure, orthostatic hypotension and cerebral congestion, and mixtures thereof.

As examples of active principles which may be contained in the medicinal product according to the invention, mention may be made of those chosen from the group of the following compounds: acetylsalicylic acid, carbamazepine, pentoxifylline, prazosine, acyclovir, nifedipine, diltiazem, naproxen, ibuprofen, flurbiprofen, ketoprofen, fenoprofen, indomethacin, diclofenac, fentiazac, oestradiol valerate, metoprolol, sulpiride, captopril, cimetidine, zidovudine, nicardipine, terfenadine, atenolol, salbutamol, carbamazepine, ranitidine, enalapril, simvastatin, fluoxetine, alprazolam, famotidine, ganciclovir, famciclovir, spironolactone, 5-asa, quinidine, perindopril, morphine, pentazocine, paracetamol, omeprazole, lansoprazole, metoclopramide, aminosalicylic acid, nalidixic acid, amoxicillin, amoxicillin and potassium clavulanate, ampicillin, ampicillin and sulbactam, azithromycin, bacampicillin, carbenicillin indanyl sodium (and other carbenicillin salts), capreomycin, cefadroxil, cefazolin, cephalexin, cephalothin, cephapirin, cephacelor, cefprozil, cephadrine, cefamandole, cefonicide, ceforanide, cefuroxime, cefixime, cefoperazone, cefotaxime, cefpodoxime, ceftaxidime, ceftibuten, ceftizoxime, ceftriaxone, cefepime, cefinetazole, cefotetan, cefoxitin, ciprofloxacine, clarithromycin, clindamycin, clofazimine, cloxacillin, cotriamoxazole, cycloserine, dicloxacillin, dirithromycin, erythromycin (and erythromycin salts such as estolate, ethylsuccinate, gluceptate, lactobionate, stearate), ethambutol-HCl and other salts, ethionamide, fosfomycin, imipenem, isoniazide, levofloxacine, lomefloxacine, loracarbef, methicillin, methenamine, metronidazole, metoclopramide, mezlocillin, nafcillin, nitrofurantoin, norfloxacin, novobiocin, ofloxacin, oxacillin, penicillin V, penicillin salts, penicillin complexes, pentamidine, piperacillin, piperacillin and tazobactam, sparfloxacin, sulphacytine, sulphamerazine, sulphamethazine, sulphamethixole, sulphasalazine, sulphisoxazole, sulphapyrizine, sulphadiazine, sulphmethoxazole, sulphapyridine, ticarcillin, ticarcillin and potassium clavulanate, trimethoprime, trimetrexate, troleanomycin, vancomycin, verapamil and mixtures thereof.

According to a particular but nonlimiting variant of the invention, the active principle(s) is (are) one of the active principle(s) with low solubility, for example chosen from the active principles as mentioned above (taken by themselves or as a mixture with one another).

The active principles to which the present invention also relates may also be nutritional and/or dietetic supplements or mixtures thereof, such as, for example, vitamins, amino acids, antioxidants or trace elements, or mixtures thereof.

Finally, the invention is also directed towards a method of therapeutic treatment, characterized in that it consists of oral administration, according to a given dosage, of the medicinal product according to the invention as defined above.

The invention will be explained more thoroughly, by the following examples, given only by way of illustration in order to fully understand the invention and to reveal its variants of implementation and/or of use.

EXAMPLES

The examples below relate to the following active principles:

| Active principle | Solubility (g/l) |
|---|---|
| Spironolactone | 0.02 |
| Lansoprazole | 0.05 |
| Nitrofurantoin | 0.3 |
| Amoxicillin trihydrate | 3.0 |
| Acyclovir | 10.0 |

Comparative Example 1 (spironolactone), Comparative Example 2 (amoxicillin trihydrate), Comparative Example 3 (nitrofurantoin) and Comparative Example 4 (carvedilol) illustrate formulations with delayed and controlled release of the active principle, obtained according to WO-A-03/03878. However, it would be advantageous to retain the lag phase while at the same time increasing the rate of release after the lag phase, in order to optimize the bioavailability and the efficacy of the active principle. The microcapsules of Comparative Examples 1 to 4 do not comprise any swelling agent.

Examples 5 (spironolactone), 6 (amoxicillin trihydrate) and 7 (nitrofurantoin) illustrate formulas according to the invention.

Examples 8, 9 and 10 (acyclovir) show the influence of the amount of swelling agent present in the formulas on the release kinetics at pH 1.4.

Examples 11, 12 and 13 (acyclovir) illustrate a nonexhaustive selection of swelling agents which may be used in the formulas according to the invention.

Example 14 (acyclovir) illustrates the preparation of microcapsules combining a wet granulation step and a coating step in a fluidized air bed.

Example 15 (acyclovir) illustrates the preparation of microcapsules combining an extrusion/spheronization step and a coating step in a fluidized air bed.

Example 16 (acyclovir) illustrates the preparation of microcapsules combining a compacting step and a coating step in a fluidized air bed.

Example 17 (acyclovir) illustrates the preparation of a medicinal product composed of the mixture of various types of microunits.

Comparative Example 1

Preparation of Microcapsules of Spironolactone Containing No Swelling Agent Step 1:

432 g of spironolactone and 48 g of low molar mass hydroxypropylcellulose (Klucel® EF/Hercules) are dispersed in 1120 g of purified water. The suspension is sprayed onto 720 g of neutral microspheres (Asahi-Kasei) in a Glatt GPCG1 spray coater.

Step 2:

43.2 g of hydrogenated cottonseed oil (Penwest) and 64.8 g of poly(methacrylicacid)(ethyl acrylate) Eudragit® L100-55 (Röhm) are dissolved under hot conditions in isopropanol. The solution is sprayed onto 492 g of microparticles prepared above.

The microcapsules obtained at the end of the second step were tested in a type II dissolutest in accordance with the European Pharmacopoeia, 4th edition, at 37° C. and with agitation at 100 rpm, in the following media:

HCl at pH 1.4

Figure 1:
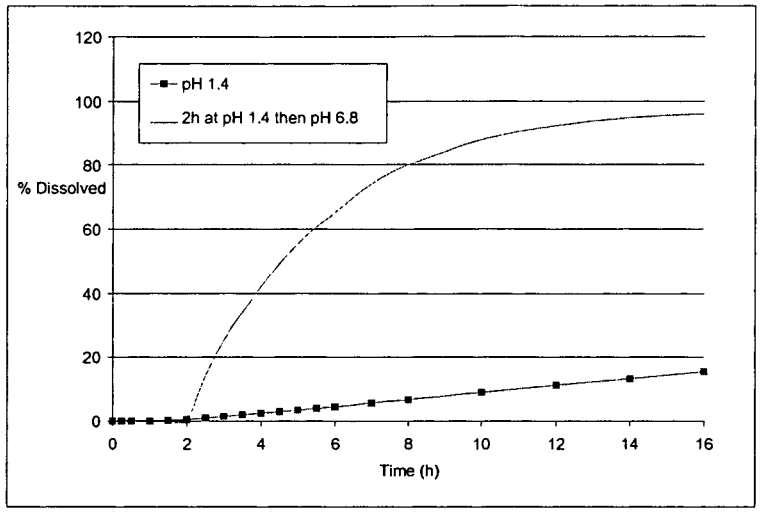
FIG. 1: In vitro release profiles for the microcapsules prepared according to Comparative Example 1.

HCl at pH 1.4 for 2 hours and then $KH_2PO_4$/NaOH buffer medium at pH 6.8 the dissolution profiles are given in FIG. 1.

It is noted that:

at pH 1.4, the release of the active principle is slow after the lag period of approximately 2 hours;

when the pH changes from 1.4 to 6.8, the release kinetics accelerate but remain slow (approximately 8 hours are required in order to release 80% of the active principle).

The novel compositions according to the invention make it possible to accelerate the release profiles at pH 1.4 and at pH 6.8, while at the same time conserving the lag phase at pH 1.4.

Comparative Example 2

Preparation of Microcapsules of Amoxicillin Trihydrate Containing No Swelling Agent Step 1:

1620 g of amoxicillin trihydrate and 180 g of low molar mass hydroxypropylcellulose (Klucel® EF (Hercules)) are dispersed in 4200 g of purified water. The suspension is sprayed onto 200 g of neutral microspheres (Asahi-Kasei) in a Glatt GPCG1 spray coater.

Step 2:

120 g of hydrogenated cottonseed oil (Penwest) and 180 g of poly(methacrylic acid)(ethyl acrylate) Acrycoat® L100D (NP Pharm) are dissolved under hot conditions in isopropanol. The solution is sprayed onto 700 g of microparticles prepared above.

The microcapsules obtained at the end of the second step were tested in a type II dissolutest in accordance with the European Pharmacopoeia, 4th edition, at 37° C. and with agitation at 100 rpm, in the following media:

HCl at pH 1.4

Figure 2:
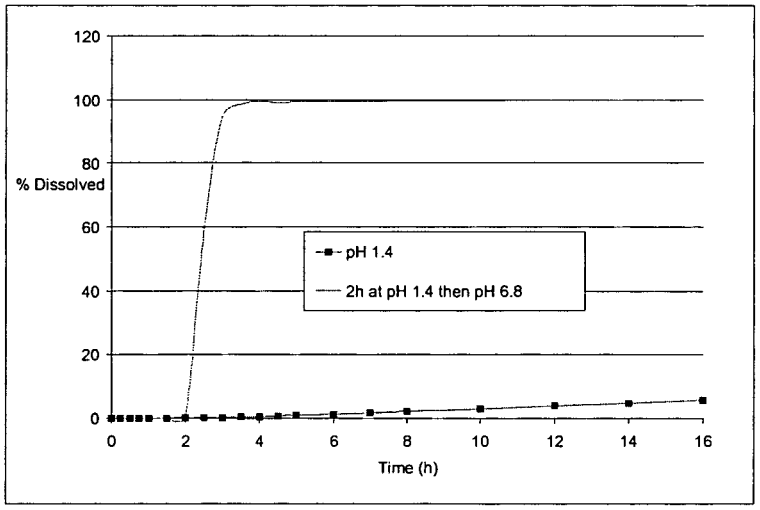
FIG. 2: In vitro release profiles for the microcapsules prepared according to Comparative Example 2.

HCl at pH 1.4 for 2 hours and then $KH_2PO_4$/NaOH buffer medium at pH 6.8 the dissolution profiles are given in FIG. 2.

It is noted that:

at pH 1.4, the release of the active principle is slow after the lag period of approximately 4 hours;

when the pH changes from 1.4 to 6.8, the release kinetics are rapid as expected.

The novel compositions according to the invention make it possible to optimize the release profiles at pH 1.4, while at the same time maintaining rapid release at pH 6.8 and conserving a lag phase at pH 1.4.

Comparative Example 3

Preparation of Microcapsules of Nitrofurantoin Containing No Swelling Agent

Step 1:

640 g of amoxicillin trihydrate and 160 g of low molar mass hydroxypropylcellulose (Klucel® EF/Hercules) are dispersed in 2400 g of purified water. The suspension is sprayed onto 200 g of neutral microspheres (Asahi-Kasei) in a Glatt GPCG1 spray coater.

Step 2:

40 g of hydrogenated cottonseed oil (Penwest), 5 g of dibutyl sebacate (Morflex) and 55 g of poly(methacrylic acid) (methyl methacrylate) Eudragit® L100 (Röhm) are dissolved under hot conditions in isopropanol. The solution is sprayed onto 900 g of microparticles prepared above.

The microcapsules obtained at the end of the second step were tested in a type II dissolutest in accordance with the European Pharmacopoeia, 4th edition, at 37° C. and with agitation at 100 rpm, in the following media:

HCl at pH 1.4

Figure 3:
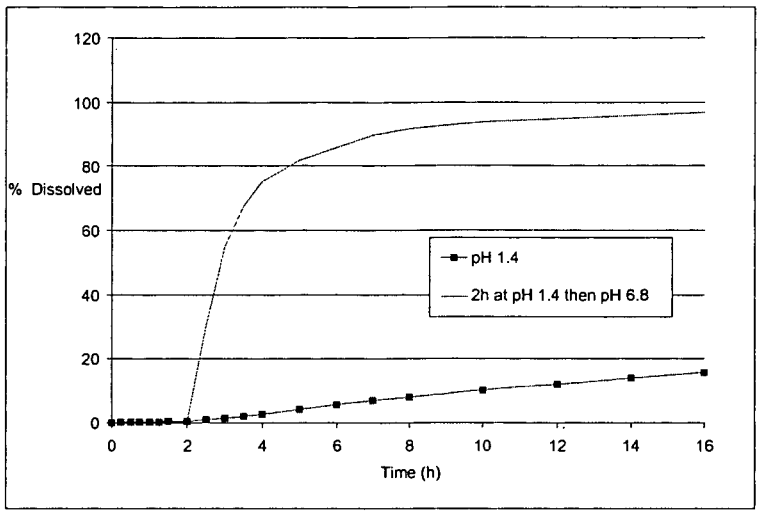
FIG. 3: In vitro release profiles for the microcapsules prepared according to Comparative Example 3.

HCl at pH 1.4 for 2 hours and then $KH_2PO_4$/NaOH buffer medium at pH 6.8 the dissolution profiles are given in FIG. 3.

It is noted that:

at pH 1.4, the release of the active principle is slow after the lag period of approximately 2 hours;

when the pH changes from 1.4 to 6.8, the release kinetics are rapid as expected.

The novel compositions according to the invention make it possible to optimize the release profiles at pH 1.4, while at the same time maintaining rapid release at pH 6.8 and conserving a lag phase at pH 1.4.

Comparative Example 4

Preparation of Microcapsules of Carvedilol Phosphate Containing No Swelling Agent 1120 g of carvedilol phosphate and 280 g of Plasdone K29/32® (ISP) are dispersed in 1120 g of purified water. The suspension is sprayed onto 600 g of neutral microspheres (Asahi-Kasei) in a Glatt GPCG1 spray coater.

100 g of hydrogenated cottonseed oil (Penwest) and 150 g of Eudragit® L100-55 (Röhm) are dissolved under hot conditions in isopropanol. The solution is sprayed onto 750 g of microparticles prepared above.

The microcapsules obtained at the end of the second step were tested in a type II dissolutest in accordance with the Pharmacopoeia, at 37° C. and with agitation at 100 rpm, in the following media:

HCl at pH 1.4

HCl at pH 1.4 for 2 hours and then $KH_2PO_4$/NaOH buffer medium at pH 6.8

Figure 4:
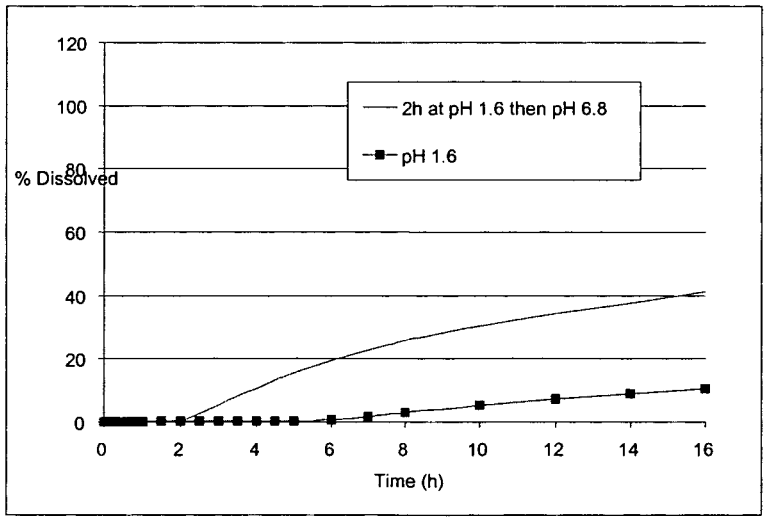
FIG. 4: In vitro release profiles for the microcapsules prepared according to Comparative Example 4.
Figure 5:
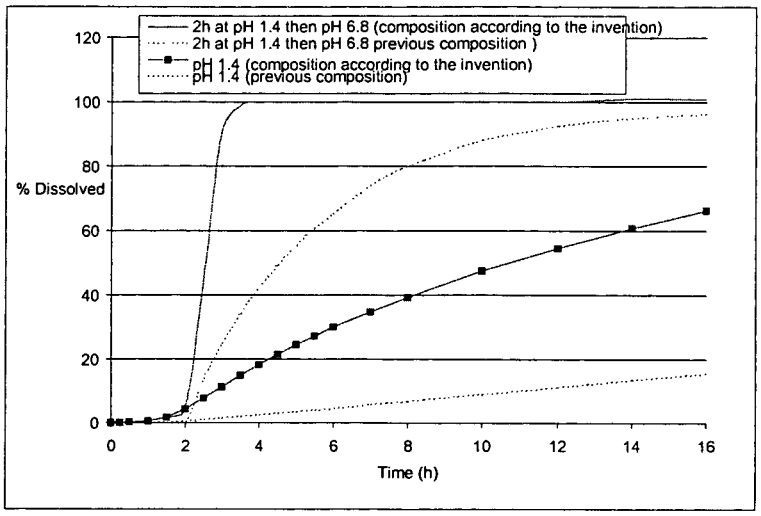
FIG. 5: In vitro release profiles for the microcapsules prepared according to Example 5 and comparison with the release profiles for the microcapsules prepared according to Comparative 1.

The dissolution profiles are given in FIG. 4 in the appendix.

It is noted that:

at pH 1.4, the release of the active principle is slow after the lag period of approximately 2 hours;

when the pH changes from 1.4 to 6.8, the release kinetics accelerate but remain slow (at 16 hours, only 40% of the active principle has been released).

Example 5

Preparation of Microcapsules of Spironolactone According to the Invention

Step 1:

216 g of spironolactone, 72 g of low molar mass hydroxypropylcellulose (Klucel® EF/Hercules), 72 g of PEG-40 hydrogenated castor oil (Cremophor RH 40/BASF) and 360 g of crospovidone (Kollidon CL/BASF) are dispersed in 1120 g of purified water. The suspension is sprayed onto 720 g of neutral microspheres (Asahi-Kasei) in a Glatt GPCG1 spray coater.

Step 2:

43.2 g of hydrogenated cottonseed oil (Penwest) and 64.8 g of poly(methacrylic acid)(ethyl acrylate) Eudragit® L100-55 (Röhm) are dissolved under hot conditions in isopropanol. The solution is sprayed onto 492 g of microparticles prepared above.

The microcapsules obtained at the end of the second step were tested in a type II dissolutest in accordance with the European Pharmacopoeia, 4th edition, at 37° C. and with agitation at 100 rpm, in the following media:

HCl at pH 1.4

HCl at pH 1.4 for 2 hours and then $KH_2PO_4$/NaOH buffer medium at pH 6.8 the dissolution profiles of Example 5 and of Comparative Example 1 are given in FIG. 4.

It is noted that:

at pH 1.4, approximately 60% of the active principle is released after a lag period of approximately 1 hour 30 min;

when the pH changes from 1.4 to 6.8, the release kinetics are rapid.

Example 6

Preparation of Microcapsules of Amoxicillin Trihydrate According to the Invention Step 1:

630 g of amoxicillin trihydrate, 90 g of povidone (plasdone® K29/32 (ISP)) and 180 g of crospovidone (Polyplasdone®/ISP) are dispersed in 2100 g of isopropanol/water (70/30 m/m) mixture. The solution is sprayed onto 100 g of neutral microspheres (Asahi-Kasei) in a Glatt® GPCG1 spray coater.

Step 2:

120 g of hydrogenated cottonseed oil (Abitec) and 160 g of poly(methacrylic acid)(ethyl acrylate) Kollicoat® MAE 100P (BASF) are dissolved under hot conditions in isopropanol. The solution is sprayed onto 700 g of microparticles prepared above.

The microcapsules obtained at the end of the second step were tested in a type II dissolutest in accordance with the European Pharmacopoeia, 4th edition, at 37° C. and with agitation at 100 rpm, in the following media:

HCl at pH 1.4

Figure 6:
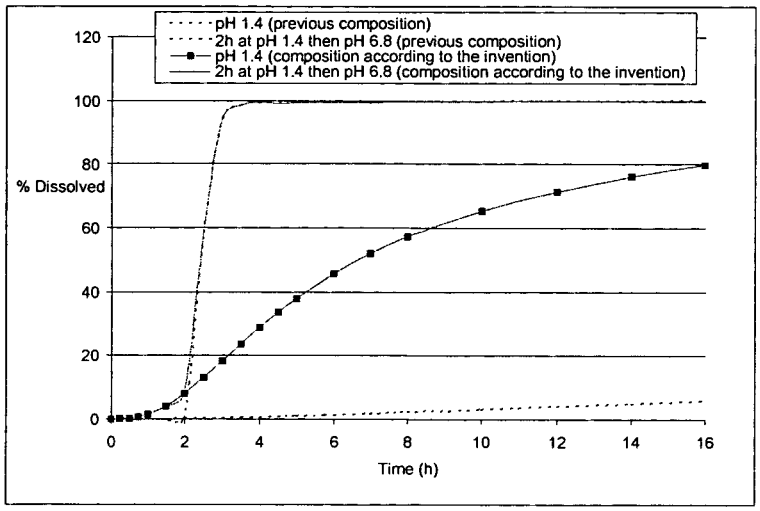
FIG. 6: In vitro release profiles for the microcapsules prepared according to Example 6 and comparison with the release profiles for the microcapsules prepared according to Comparative 2.

HCl at pH 1.4 for 2 hours and then $KH_2PO_4$/NaOH buffer medium at pH 6.8 the dissolution profiles of Example 6 and of Comparative Example 2 are given in FIG. 6.

It is noted that, with the composition according to the invention:

the release of the active principle at pH 1.4 was accelerated (guaranteeing triggering of the system after a given amount of time and release of a sufficient amount of active agent, this release taking place over times compatible with the absorption times for the active principles in the organism);

when the pH changes from 1.4 to 6.8, rapid release kinetics are maintained.

Example 7

Preparation of Microcapsules of Nitrofurantoin According to the Invention

Step 1:

400 g of nitrofurantoin, 200 g of povidone (plasdone® K29/32/ISP), 50 g of PEG-40 hydrogenated castor oil (BASF) and 350 g of crospovidone (Polyplasdone®/ISP) are suspended in 2500 g of purified water. The solution is sprayed onto 1000 g of neutral microspheres (Asahi-Kasei) in a Glatt® GPCG1 spray coater.

Step 2:

120 g of hydrogenated cottonseed oil (Abitec) and 160 g of poly(methacrylic acid)(ethyl acrylate) Acrycoat® L100D (NP Pharm) are dissolved under hot conditions in isopropanol. The solution is sprayed onto 700 g of microparticles prepared above.

The microcapsules obtained at the end of the second step were tested in a type II dissolutest in accordance with the European Pharmacopoeia, 4th edition, at 37° C. and with agitation at 100 rpm, in the following media:

HCl at pH 1.4

Figure 7:
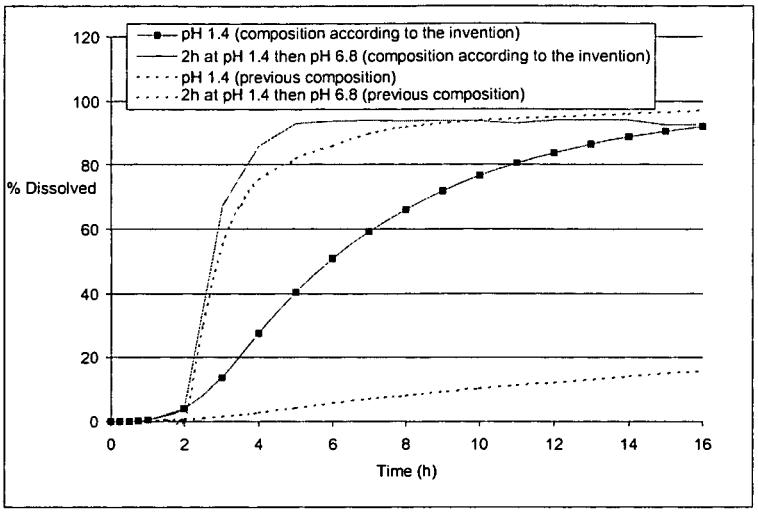
FIG. 7: In vitro release profiles for the microcapsules prepared according to Example 7 and comparison with the release profiles for the microcapsules prepared according to Comparative 3.

HCl at pH 1.4 for 2 hours and then $KH_2PO_4$/NaOH buffer medium at pH 6.8 the dissolution profiles of Example 7 and of Comparative Example 3 are given in FIG. 7.

It is noted that, with the composition according to the invention:

the release of the active principle at pH 1.4 was accelerated (guaranteeing triggering of the system after a given period of time and release of a sufficient amount of active agent, this release taking place over times compatible with the absorption times for the active principles in the organism);

when the pH changes from 1.4 to 6.8, rapid release kinetics are maintained.

Comparative Example 8

Preparation of Microcapsules of Acyclovir Containing No Swelling Agent

Step 1:

75 g of acyclovir and 75 g of povidone (Plasdone® K29/32/ISP) are dissolved in 833 g of isopropanol. The solution is sprayed onto 850 g of neutral microspheres (NP Pharm) in a Glatt® GPCG3 spray coater.

Step 2:

93.3 g of hydrogenated soybean oil (Abitec) and 140 g of poly(methacrylic acid)(methyl methacrylate) Eudragit® L100 (Röhm) are dissolved under hot conditions in isopropanol. The solution is sprayed onto 700 g of microparticles prepared above.

Example 9

Preparation of Microcapsules of Acyclovir Containing a Small Amount of Swelling Agent (Crospovidone®)

Step 1:

375 g of acyclovir, 50 g of low molar mass hydroxypropylcellulose (Klucel® EF (Hercules)) and 75 g of crospovidone (Polyplasdone®/ISP) are suspended in 1200 g of purified water. The solution is sprayed onto 500 g of neutral microspheres (NP Pharm) in a Glatt® GPCG3 spray coater.

Step 2:

100 g of hydrogenated cottonseed oil (Penwest) and 150 g of poly(methacrylic acid)(ethyl acrylate) Eudragit® L100-55 (Röhm) are dissolved under hot conditions in ethanol. The solution is sprayed onto 750 g of microparticles prepared above.

Example 10

Preparation of Microcapsules of Acyclovir Containing a Larger Amount of Swelling Agent (Crospovidone®)

Step 1:

300 g of acyclovir, 50 g of low molar mass hydroxypropylcellulose, Klucel® EF (Hercules), and 150 g of crospovidone (Polyplasdone®/ISP) are suspended in 1200 g of purified water. The solution is sprayed onto 500 g of neutral microspheres (NP Pharm) in a Glatt® GPCG3 spray coater.

Step 2:

100 g of hydrogenated cottonseed oil (Penwest) and 150 g of poly(methacrylic acid)(ethyl acrylate) Eudragit® L100-55 (Röhm) are dissolved under hot conditions in ethanol. The solution is sprayed onto 750 g of microparticles prepared above.

The microcapsules obtained at the end of the second step in Comparative Examples 8, 9 and 10 were tested in a type II dissolutest in accordance with the European Pharmacopoeia, 4th edition, at 37° C. and with agitation at 100 rpm, in the following media:

HCl at pH 1.4

Figure 8:
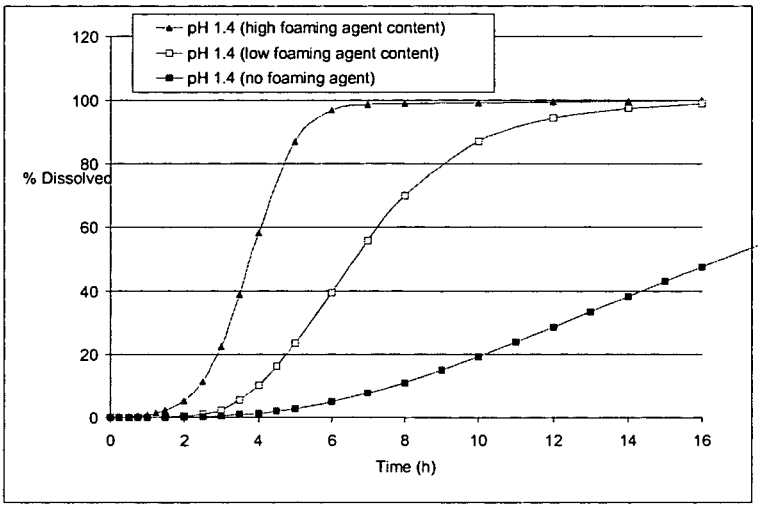
FIG. 8: Release profiles for the microcapsules prepared according to Examples 8, 9 and 10 at pH 1.4.
Figure 9:
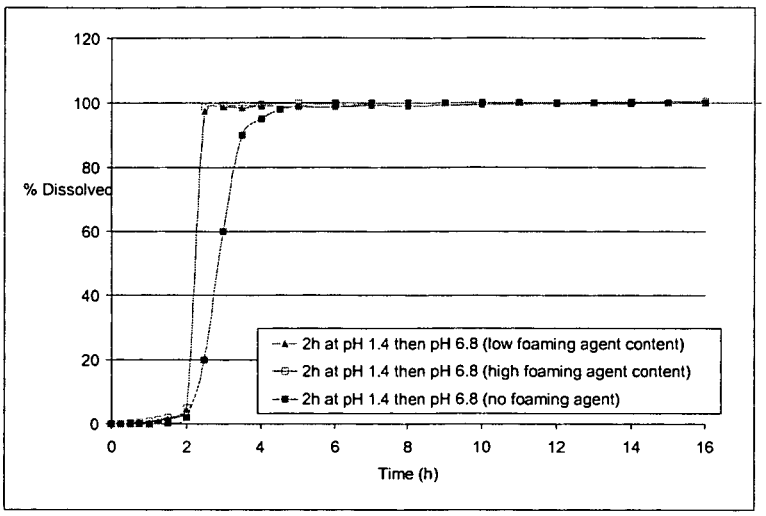
FIG. 9: Release profiles for the microcapsules prepared according to Examples 8, 9 and 10, measured for 2 h at pH 1.4 and then at pH 6.8.

HCl at pH 1.4 for 2 hours and then $KH_2PO_4$/NaOH buffer medium at pH 6.8 the dissolution profiles of Examples 8, 9 and 10 are given in FIGS. 8 and 9.

It is noted that:

a broad range of kinetics can be obtained at pH 1.4 according to the amount of swelling agent incorporated into the formulation;

the release at pH 6.8 remains rapid whatever the composition under consideration.

Example 11

Preparation of Microcapsules of Acyclovir Containing a Swelling Agent (Sodium Croscarmellose)

Step 1:

300 g of acyclovir, 50 g of low molar mass hydroxypropylcellulose, Klucel® EF (Hercules), and 150 g of sodium croscarmellose (Ac-Di-Sol®/FMC) are suspended in 1200 g of purified water. The solution is sprayed onto 500 g of neutral microspheres (NP Pharm) in a Glatt® GPCG1 spray coater.

Step 2:

100 g of hydrogenated cottonseed oil (Penwest) and 100 g of poly(methacrylic acid)(ethyl acrylate) Eudragit® L100-55 (Röhm) are dissolved under hot conditions in ethanol. The solution is sprayed onto 750 g of microparticles prepared above.

Example 12

Preparation of Microcapsules of Acyclovir Containing a Swelling Agent (Hydroxypropylmethylcellulose)

Step 1:

300 g of acyclovir, 50 g of low molar mass hydroxypropylcellulose, Klucel® EF (Hercules), and 150 g of hydroxypropylmethylcellulose (Pharmacoat 615/Shin-Etsu) are suspended in 1200 g of purified water. The solution is sprayed onto 500 g of neutral microspheres (NP Pharm) in a Glatt® GPCG1 spray coater.

100 g of hydrogenated cottonseed oil (Penwest), 100 g of poly(methacrylic acid)(ethyl acrylate) Eudragit® L100-55 (Röhm) and 50 g of poly(methacrylic acid)(methyl methacrylate) Eudragit® S100 (Röhm) are dissolved under hot conditions in ethanol. The solution is sprayed onto 750 g of microparticles prepared above.

Example 13

Preparation of Microcapsules of Acyclovir Containing a Swelling Agent (Povidone of Molar Mass Mw=1,000,000 g/mol)

Step 1:

350 g of acyclovir, 50 g of low molar mass hydroxypropylcellulose (Klucel® EF (Hercules)) and 100 g of high molar mass povidone (Kollidon® 90 (BASF)) are suspended in 1200 g of purified water. The solution is sprayed onto 500 g of neutral microspheres (NP Pharm) in a Glatt® GPCG1 spray coater.

Step 2:

100 g of hydrogenated cottonseed oil (Penwest), 50 g of poly(methacrylic acid)(ethyl acrylate) Eudragit® L100-55 (Röhm) and 100 g of poly(methacrylic acid)(methyl methacrylate) Eudragit® S100 (Röhm) are dissolved under hot conditions in ethanol. The solution is sprayed onto 750 g of microparticles prepared above.

The microcapsules obtained at the end of the second step of Examples 10, 11, 12 and 13 were tested in a type II dissolutest in accordance with the European Pharmacopoeia, 4th edition, at 37° C. and with agitation of 100 rpm at pH 1.4.

Figure 10:
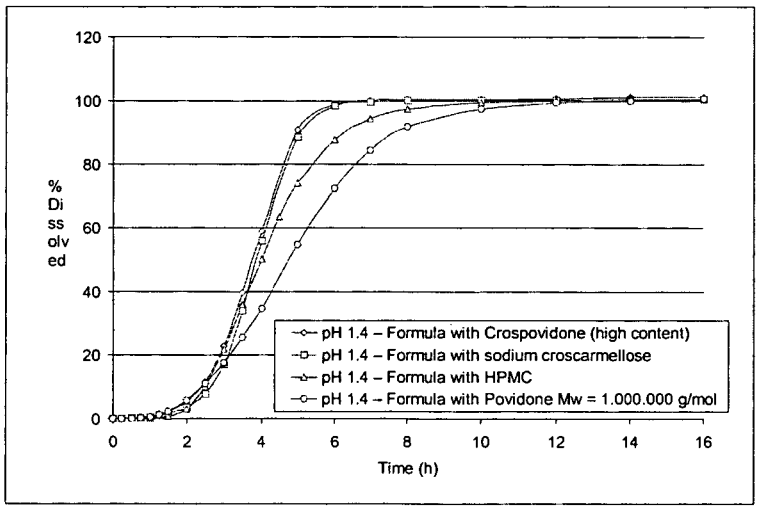
FIG. 10: Release profiles for the microcapsules prepared according to Examples 10, 11, 12 and 13 at pH 1.4.

The dissolution profiles are given in FIG. 10.

Example 14

Preparation of Microcapsules of Acyclovir Containing a Swelling Agent (Granulation+Spray-Coating)

Step 1:

700 g of acyclovir, 50 g of povidone (Plasdone®/ISP) and 250 g of crospovidone (Polyplasdone®/ISP) are dry-mixed beforehand in a laboratory granulator (Lodige) for 5 minutes. This pulverulent mixture is then granulated with water (200 g). The granules are dried at 40° C. in a ventilated oven, and then sized on a 500 μm screen. The 200-500 μm fraction is selected by sieving.

Step 2:

100 g of hydrogenated palm oil (Huls), 100 g of poly (methacrylic acid)(ethyl acrylate) Acrycoat® L100D and 50 g of poly(methacrylic acid)(methyl methacrylate) Acrycoat® S100 (NP Pharm) are dissolved under hot conditions in isopropanol. The solution is sprayed onto 750 g of microparticles prepared above.

The microcapsules obtained at the end of the second step of Example 13 were tested in a type II dissolutest in accordance with the European Pharmacopoeia, 4th edition, at 37° C. and with agitation at 100 rpm, in the following media:

HCl at pH 1.4

HCl at pH 1.4 for 2 hours and then $KH_2PO_4$NaOH buffer medium at pH 6.8

Figure 11:
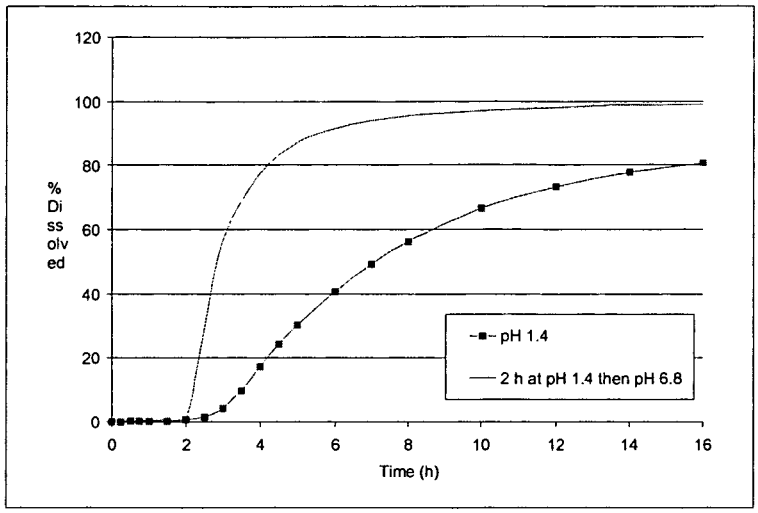
FIG. 11: Release profiles for the microcapsules prepared according to Example 14.

The dissolution profiles are given in FIG. 11.

Example 15

Preparation of Microcapsules of Acyclovir Containing a Swelling Agent (Extrusion/Spheronization+Spray Coating)

Step 1:

700 g of acyclovir, 50 g of povidone (Plasdone®/ISP) and 250 g of crospovidone (Kollidon® CL/BASF) are premixed with 150 g of water in a laboratory mixer (Kitchen-Aid) for 5 minutes. This pasty mixture is extruded through a 0.5 mm screen using an Extruder 20 (Caleva). The filaments obtained are then spheronized using a Spheronizer 250 (Caleva). The particles obtained are dried at 40° C. in a fluidized air bed. The 300-700 μm fraction is selected by sieving.

Step 2:

100 g of hydrogenated palm oil (Huls), 100 g of poly (methacrylic acid)(ethyl acrylate) Acrycoat® L100D and 50 g of poly(methacrylic acid)(methyl methacrylate) Acrycoat® S100 (NP Pharm) are dissolved under hot conditions in isopropanol. The solution is sprayed onto 750 g of microparticles prepared above.

The microcapsules obtained at the end of the second step of Example 14 were tested in a type II dissolutest in accordance with the Pharmacopoeia, 4th edition, at 37° C. and with agitation at 100 rpm, in the following media:

HCl at pH 1.4

HCl at pH 1.4 for 2 hours and then $KH_2PO_4$/NaOH buffer medium at pH 6.8

Figure 12:
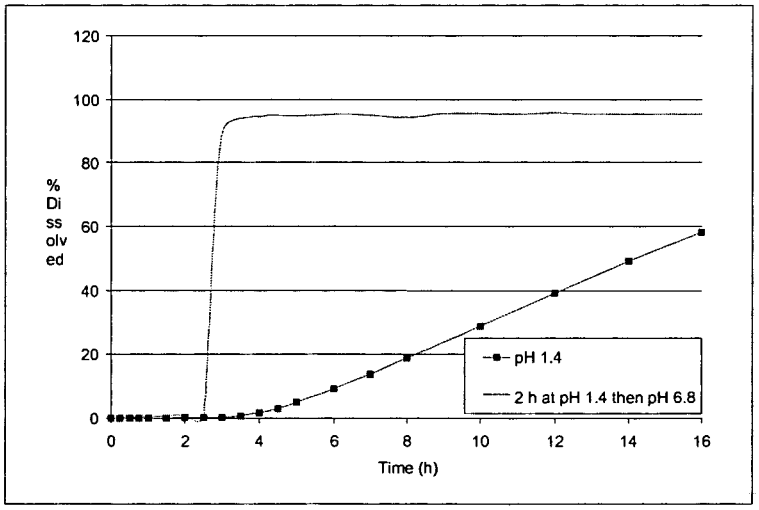
FIG. 12: Release profiles for the microcapsules prepared according to Example 15.

The dissolution profiles are given in FIG. 12.

Example 16

Preparation of Microcapsules of Acyclovir Containing a Swelling Agent (Compacting+Spray-Coating)

Step 1:

590 g of acyclovir, 10 g of magnesium stearate and 400 g of crospovidone are mixed using a laboratory mixer (Kitchen-Aid type) for 5 minutes. This mixture is then compacted using an Alexenderwerk WP120 laboratory compactor. The product obtained is then granulated using an Erweka oscillating granulator equipped with a 500 μm screen. The 100-500 μm fraction of the product obtained is selected by sieving.

Step 2:

100 g of hydrogenated palm oil (Huls), 100 g of poly (methacrylic acid)(ethyl acrylate) Acrycoat L100D and 50 g of poly(methacrylic acid)(methyl methacrylate) Acrycoat® S100 (NP Pharm) are dissolved under hot conditions in isopropanol. The solution is sprayed onto 750 g of microparticles prepared above.

The microcapsules obtained at the end of the second step of Example 14 were tested in a type II dissolutest in accordance with the Pharmacopoeia, 4th edition, at 37° C. and with agitation at 100 rpm, in the following media:

HCl at pH 1.4

HCl at pH 1.4 for 2 hours and then $KH_2PO_4$/NaOH buffer medium at pH 6.8

Figure 13:
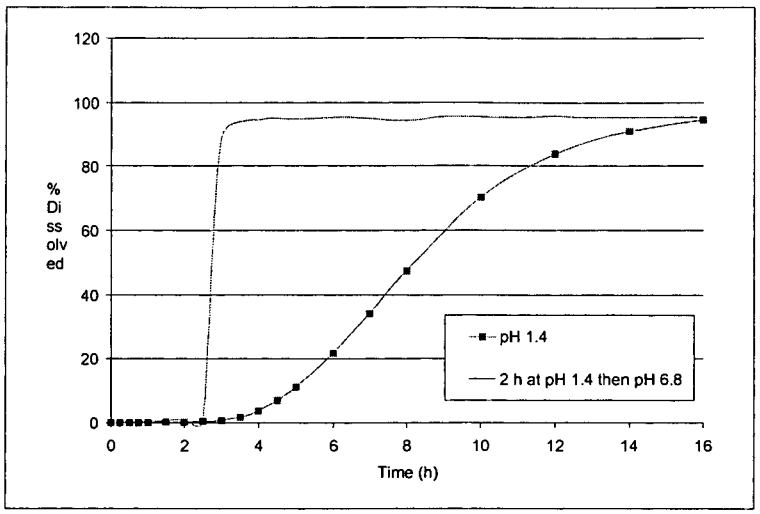
FIG. 13: Release profiles for the microcapsules prepared according to Example 16.

The dissolution profiles are given in FIG. 13.

Example 17

Mixture of Microunits Having Various Release Profiles

Various microunits of acyclovir are prepared, in which:

25% by weight of the acyclovir is in the form of immediate-release microunits as obtained at the end of the first step of Example 12, 25% of the acyclovir is in the form of delayed and prolonged-release microunits as obtained at the end of the second step of Example 10, and 50% of the acyclovir is in the form of delayed and prolonged-release microcapsules as obtained at the end of the second step of Example 12.

The microcapsules of Example No. 10 begin to rapidly release their content beyond pH≥5.5 (use of Eudragit® L100-55).

The microcapsules of Example No. 12 begin to rapidly release their content beyond pH>6.5 (use of 67% Eudragit® L100-55 and 33% Eudragit® S100).

Figure 14:
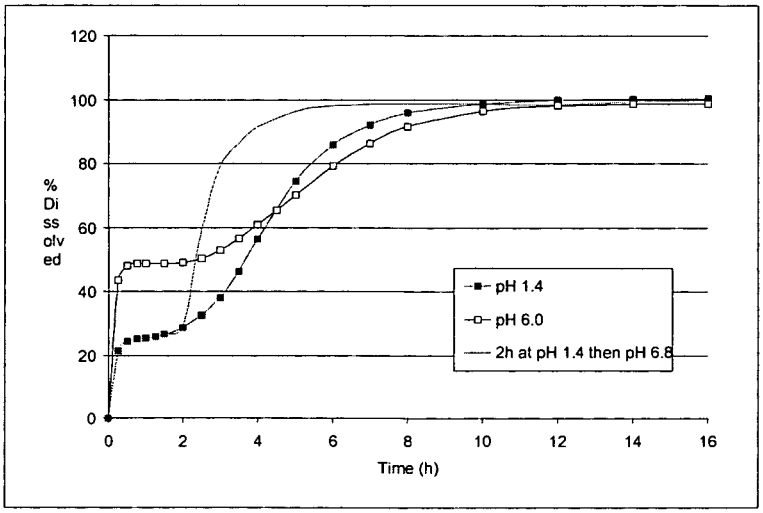
FIG. 14: Release profiles for the microcapsules prepared according to Example 17.

The profiles are given in FIG. 14 and show that various release phases are obtained, which optimizes the release of an active principle in front of its window of absorption.

The invention claimed is:

1. An oral medicinal product comprising a plurality of microcapsules with modified release of active principle(s), wherein at least one [of said microcapsules] *microcapsule* individually comprises:

a microparticle comprising at least one active principle having a solubility of less than 20 g/L [(with the exclusion of carvedilol)] and a swelling agent; and one coating on said microparticle making possible the modified release of the at least one active principle, said release being controlled by means of two distinct triggering mechanisms, wherein a first triggering mechanism is based on a variation in pH and wherein a second triggering mechanism is based on release of the at least one active principle after a predetermined period of residence in the stomach, wherein said coating confers on the microcapsules an in vitro dissolution behavior such that: at constant pH 1.4, the dissolution profile comprises a lag phase of less than or equal to 7 hours, and a change from pH 1.4 to pH 7.0 results in a release phase that begins without any lag time;

wherein said swelling agent is capable of increasing the permeability of the coating for modified release of the *at least one* active principle;

wherein said swelling agent is selected from the group consisting of crosslinked polyvinylpyrrolidones, crosslinked carboxyalkylcelluloses, polacrilin potassium and mixtures thereof; *and*

[and] wherein the fraction by weight of the at least one active [principle(s)] *principle* released during the lag phase is less than or equal to 15% by weight per hour.

2. The medicinal product according to claim 1, wherein the swelling agent is chosen from those that allow the microcapsules to release in vitro at least 50% by weight of the *at least one* active principle after 16 hours at pH 1.4.

3. The medicinal product according to claim 1, wherein the swelling agent is in the form of microparticles with a mean diameter of between 5 and 200 μm.

4. The medicinal product according to claim 1, wherein the swelling agent is present in an amount of between 3 and 40% by weight relative to the total mass of the microcapsules.

5. The medicinal product according to claim 1, further comprising at least one wetting agent, contained in the microparticle, selected from the group consisting of anionic surfactants, nonionic surfactants, and mixtures thereof.

6. The medicinal product according to claim 1, wherein the microcapsules are capable of releasing in vitro at least 80% by weight of the *at least one* active [principle(s)] *principle* after 12 hours at pH=7.0.

7. The medicinal product according to claim 1, wherein at least one [of said modified-release microcapsules] *microcapsule* comprises a microparticle comprising a neutral core, and at least one active layer comprising at least one active principle.

8. The medicinal product according to claim 1, wherein [at least one of] the coating making possible *the* modified release of the *at least one* active [principle(s)] *principle* comprises a composite material comprising: at least one hydrophilic polymer A carrying groups that are ionized at neutral pH and at least one hydrophobic compound B; representing a mass fraction of ≤40% weight relative to the total mass of the microcapsules; and wherein the microcapsules have a mean diameter of less than 2000 μm.

9. The medicinal product according to claim 8, wherein the weight ratio of B/A is between 0.2 and 1.5; and the hydrophobic compound B is selected from products that are crystalline in the solid state and that have a melting point $T_{mB} \geq 40°$ C.

10. The medicinal product according to either of claims 8 and 9, wherein the hydrophilic polymer A is selected from the group consisting of copolymers of (meth)acrylic acid, copolymers of (meth)acrylic acid alkyl ester, cellulose phthalate, cellulose acetate phthalate, hydroxypropylmethylcellulose phthalate, hydroxypropylmethylcellulose acetates succinate; and mixtures thereof.

11. The medicinal product according to one of claims 8 and 9, wherein the compound B is selected from the group consisting of vegetable waxes, mixtures of vegetable waxes, hydrogenated vegetable oils, mixtures of hydrogenated vegetable oils, diesters of glycerol and fatty acid, triesters of glycerol and fatty acid, yellow wax, lanolin, cetyl alcohol, and mixtures thereof.

12. The medicinal product according to claim 11, wherein compound B is selected from the group consisting of: hydrogenated cottonseed oil, hydrogenated soybean seed oil, hydrogenated palm oil, glyceryl behenate, hydrogenated castor oil, tristearin, tripalmitin, trimyristin, yellow wax, hard fat, fat that is useful as suppository bases, anhydrous dairy fats, lanolin, glyceryl palmitostearate, glyceryl stearate, lauryl macrogolglycerides, cetyl alcohol, polyglyceryl diisostearate, and mixtures thereof.

13. The medicinal product according to claim 8 wherein the coating making possible the *modified* release of the at least one active [principle(s) of the microcapsules with modified release of active] principle comprises a single coating film comprising the composite material AB.

14. The medicinal product according to claim 1, said product comprising a mixture of more than one population of microunits, [each microunit containing at least one] *the populations of microunits comprising* active principle(s), [(with the exclusion of carvedilol),] and wherein the populations differ from one another in that they have different in vitro dissolution profiles for at least one pH value of between 1.4 and 7.4.

15. The medicinal product according to claim 14, wherein each population of microunits comprises a population of microcapsules with modified release of active principle(s), and wherein at least one population of microcapsules with modified release of active principle(s) differs from at least one other population of microcapsules with modified release of active principle(s) through their respective triggering pHs.

16. The medicinal product according to claim 14, comprising at least two populations of microunits, wherein each population of microunits comprises a population of microcapsules with modified release of active principle(s), and wherein at least one population of microcapsules with modified release of active principle(s) differs from at least one other population of microcapsules with modified release of active principle(s) through their respective triggering times.

17. The medicinal product according to claim 14, wherein said product comprises:

i. at least one population of microunits containing active principle(s) that allows immediate release of the active principle(s);

ii. at least one population P1 of microcapsules with modified release of active principle(s); and iii. at least one population P2 of microcapsules with modified release of active principle(s);

and wherein the respective triggering pHs of P1 and of P2 differ by at least 0.5 of a pH unit.

18. The medicinal product according to claim 14, wherein the respective triggering pH of each of the more than one population of [microcapsules with modified release of active principle(s)] *microunits* is between 5 and 7.

19. The medicinal product according to claim 14, wherein said product comprises:

i. at least one population of microunits containing active principle(s) and allowing immediate release of the active principle(s);

ii. at least one population P1' of microunits containing active principle(s), wherein the P1' population of microunits comprises microcapsules with modified release of the active principle(s) having a triggering pH [is] equal to 5.5; and iii. at least one population P2' of microunits containing active principle(s), wherein the P2' population of microunits comprises microcapsules with modified release of the active principle(s) having a triggering pH equal to 6.0 or 6.5.

20. The medicinal product according to claim 14, wherein said product has the following in vitro release profile: less than 20% of the active principle(s) is released after 2 hours at pH=1.4; *and* at least 50% of the active principle(s) is released after 16 hours at pH=1.4.

21. The medicinal product according to claim 14, wherein said product comprises at least one population of microunits containing active principle(s) with immediate release, the behavior of which in an in vitro dissolution test is such that at least 80% of the active principle(s) is released in 1 hour at any pH of between 1.4 and 7.4.

22. The medicinal product according to claim 14, wherein the microunits containing active principle(s) contain active principle(s) in an amount that is between 5 and 80% by weight on a dry basis relative to the total mass of the microunits.

23. The medicinal product according to claim 1, wherein the product is provided in the form of a single daily oral dose comprising from 5,000 to 500,000 microcapsules with modified release of active principle(s).

24. The medicinal product according to claim 1, wherein at least one of the at least one active [principle(s)] *principle* is selected from the group consisting of: antiulcer agents, antidiabetic agents, anticoagulants, antithrombics, blood lipid-lowering agents, [antiarythmics] *antiarrhythmics*, vasodilators, anti-angina agents, antihypertensives, vasoprotective agents, fertility promoters, inducers and inhibitors of uterine labor, contraceptives, antibiotics, antifungal agents, antiviral agents, anticancer agents, anti-inflammatories, analgesics, antiepileptics, antiparkinsonian agents, neuroleptics, hypnotics, anxiolytics, psychostimulants, antimigraine agents, antidepressants, antitussives, antihistamines or antiallergic agents, agents for combating congestive heart failure, angina pectoris, left ventricular hypertrophy, cardiac [arythmias] *arrhythmias*, myocardial infarctions, reflex tachycardia, ischaemic heart disease, atheromatosis, hypertension related to diabetes mellitus, portal hypertension, dizziness, bradycardia, arterial hypotension, hydrosodic retention, acute kidney failure, orthostatic hypotension, cerebral congestion, and mixtures thereof.

25. The medicinal product according to claim 1, wherein at least one of the at least one active [principle(s)] *principle* is selected from the group of products consisting of: acetylsalicylic acid, carbamazepine, pentoxifylline, prazosine, acyclovir, nifedipine, diltiazem, naproxen, ibuprofen, flurbiprofen, ketoprofen, fenoprofen, indomethacin, diclofenac, fentiazac, oestradiol valerate, metoprolol, sulpiride, captopril, cimetidine, zidovudine, nicardipine, terfenadine, atenolol, salbutamol, carbamazepine, ranitidine, enalapril, simvastatin, fluoxetine, alprazolam, famotidine, ganciclovir, famciclovir, spironolactone, 5-asa, quinidine, perindopril, morphine, pentazocine, paracetamol, omeprazole, lansoprazole, metoclopramide, aminosalicylic acid, nalidixic acid, amoxicillin, amoxicillin and potassium clavulanate, ampicillin, ampicillin and sulbactam, azithromycin, bacampicillin, carbenicillin indanyl sodium [(and other carbenicillin salts)], *other carbenicillin salts,* capreomycin, cefadroxil, cefazolin, cephalexin, cephalothin, cephapirin, cephacelor, cefprozil, cephadrine, cefamandole, cefonicide, ceforanide, cefuroxime, cefixime, cefoperazone, cefotaxime, cefpodoxime, ceftaxidime, ceftibuten, ceftizoxime, ceftriaxone, cefepime, cefinetazole, cefotetan, cefoxitin, ciprofloxacine, clarithromycin, clindamycin, clofazimine, cloxacillin, cotriamoxazole, cycloserine, dicloxacillin, dirithromycin, erythromycin [(and erythromycin salts such as estolate, ethylsuccinate, gluceptate, lactobionate, stearate)], *erythromycin estolate, erythromycin ethylsuccinate, erythromycin gluceptate, erythromycin lactobionate, erythromycin stearate,* ethambutol-HCl [and], other *ethambutol* salts, ethionamide, fosfomycin, imipenem, isoniazide, levofloxacine, lomefloxacine, loracarbef, methicillin, methenamine, metronidazole, metoclopramide, mezlocillin, nafcillin, nitrofurantoin, norfloxacin, novobiocin, ofloxacin, oxacillin, penicillin V, penicillin salts, penicillin complexes, pentamidine, piperacillin, piperacillin and tazobactam, sparfloxacin, sulphacytine, sulphamerazine, sulphamethazine, sulphamethixole, sulphasalazine, sulphisoxazole, sulphapyrizine, sulphadiazine, sulphmethoxazole, sulphapyridine, ticarcillin, ticarcillin and potassium clavulanate, trimethoprime, trimetrexate, troleanomycin, vancomycin, verapamil and mixtures thereof.

26. A method of therapeutic treatment, wherein the treatment comprises oral administration, according to a given dosage, of a medicinal product of claim 1.

27. The medicinal product according to claim 14, wherein one population of microunits consists of microunits that allow immediate release of the active principle(s).

28. The medicinal product according to claim 5, wherein the at least one wetting agent is selected from the group consisting of alkali metal salts of fatty acids, alkaline-earth metal salts of fatty acids, polyoxyethylenated oils, polyoxyethylene-polyoxypropylene copolymers, polyoxyethylenated esters of sorbitan, polyoxyethylenated derivatives of castor oil, calcium stearate, magnesium stearate, aluminum stearate, zinc stearate, sodium stearylfumarate, glyceryl behenate, and mixtures thereof.

*29. A composition comprising a plurality of microcapsules,*

*wherein at least one microcapsule individually comprises:*

*a microparticle comprising at least one active principle having a solubility of less than 20 g/L and a swelling agent; and*

*one coating on said microparticle making possible modified release of the at least one active principle,*

*wherein said coating confers on the microcapsules an in vitro dissolution behavior such that: at constant pH 1.4, the dissolution profile comprises a lag phase of less than or equal to 7 hours, and a change from pH 1.4 to pH 7.0 results in a release phase that begins without any lag time;*

*wherein said swelling agent is capable of increasing the permeability of the coating for modified release of the at least one active principle;*

*wherein said swelling agent is selected from the group consisting of crosslinked polyvinylpyrrolidones, crosslinked carboxyalkylcelluloses, polacrilin potassium and mixtures thereof;*

*and wherein the fraction by weight of the at least one active principle released during the lag phase is less than or equal to 15% by weight per hour.*

*30. The composition of claim 29, wherein the composition is an oral pharmaceutical form in the form of a tablet, powder, sachet, liquid suspension, or capsule.*

*31. The composition of claim 29, wherein said swelling agent is selected from the group consisting of crosslinked carboxymethylcelluloses.*

*32. The composition of claim 31, wherein said swelling agent is sodium croscarmellose.*

*33. The composition of claim 29, wherein said swelling agent allows the microcapsules to release in vitro at least 50% by weight of the at least one active principle after 16 hours at pH 1.4.*

*34. The composition of claim 29, wherein the swelling agent is in the form of microparticles with a mean diameter of between 5 and 200 μm.*

*35. The composition of claim 29, wherein the swelling agent is in the form of microparticles with a mean diameter of between 10 and 50 μm.*

*36. The composition of claim 29, wherein said swelling agent is present in an amount of 4 to 30% by weight relative to the total mass of the microcapsules.*

*37. The composition of claim 29, wherein said swelling agent is present in an amount of 4 to 30% by weight relative to the total mass of the microcapsules.*

38. The composition of claim 29, wherein said swelling agent is present in an amount of 5 to 25% by weight relative to the total mass of the microcapsules.

39. The composition of claim 29, further comprising at least one wetting agent, contained in the microparticle, said at least one wetting agent selected from the group consisting of anionic surfactants, nonionic surfactants, and mixtures thereof.

40. The composition of claim 39, wherein said at least one wetting agent is selected from the group consisting of: alkali metal salts of fatty acids, alkaline-earth metal salts of fatty acids, and combinations thereof.

41. The composition of claim 40, wherein said at least one wetting agent is selected from the group consisting of: alkali metal salts of stearic acid, alkali metal salts of oleic acid alkaline-earth metal salts of stearic acid, alkaline-earth metal salts of oleic acid and combinations thereof.

42. The composition of claim 40, wherein said at least one wetting agent is selected from the group consisting of: polyoxyethylenated oils, polyoxyethylene-polyoxypropylene copolymers, polyoxyethylenated esters of sorbitan, polyoxyethylenated derivatives of castor oil, stearates, calcium stearate, magnesium stearate, aluminum stearate, zinc stearate, stearyl fumarates, sodium stearyl fumarate, glyceryl behenate, and combinations thereof.

43. The composition of claim 42, wherein said at least one wetting agent is polyoxyethylenated hydrogenated castor oil.

44. The composition of claim 29, wherein said at least one microcapsule releases in vitro at least 80% by weight of the at least one active principle after 12 hours at pH=7.0.

45. The composition of claim 29, wherein at least one microcapsule comprises a microparticle comprising a neutral core, and at least one active layer comprising at least one active principle.

46. The composition of claim 45, wherein said neutral core comprises sucrose, dextrose, lactose, or combinations thereof.

47. The composition of claim 45, wherein said neutral core comprises a cellulose microsphere.

48. The composition of claim 45, wherein said neutral core has a mean diameter of between 1 and 800 μm.

49. The composition of claim 45, wherein said neutral core has a mean diameter of between 20 and 500 μm.

50. The composition of claim 45, wherein said swelling agent is contained in said at least one active layer.

51. The composition of claim 45, wherein said at least one active layer comprises the at least one active principle, at least one swelling agent, at least one binder, and at least one surfactant.

52. The composition of claim 29, wherein said coating represents a mass fraction of less than or equal to 30% by weight relative to the total mass of the microcapsules.

53. The composition of claim 29, wherein said coating comprises a composite material, wherein the composite material comprises: at least one hydrophilic polymer A carrying groups that are ionized at neutral pH and at least one hydrophobic compound B; and wherein said coating represents a mass fraction of less than or equal to 40% by weight relative to the total mass of the microcapsules; and wherein the microcapsules have a mean diameter of less than 2000 μm.

54. The composition of claim 53, wherein the weight ratio of B to A is between 0.2 and 1.5; and the hydrophobic compound B is selected from products that are crystalline in the solid state and that have a melting point $T_{mB}$ more than or equal to 40° C.

55. The composition of claim 53, wherein the hydrophilic polymer A is selected from the group consisting of: copolymers of (meth)acrylic acid, copolymers of (meth)acrylic acid alkyl ester, cellulose phthalate, cellulose acetate phthalate, hydroxypropylmethylcellulose phthalate, hydroxypropylmethylcellulose acetate succinate and mixtures thereof.

56. The composition of claim 53, wherein the compound B is selected from the group consisting of vegetable waxes, mixtures of vegetable waxes, hydrogenated vegetable oils, mixtures of hydrogenated vegetable oils, diesters of glycerol and fatty acid, triesters of glycerol and fatty acid, yellow wax, lanolin, cetyl alcohol and mixtures thereof.

57. The composition of claim 56, wherein the compound B is selected from the group consisting of: hydrogenated cottonseed oil, hydrogenated soybean seed oil, hydrogenated palm oil, glyceryl behenate, hydrogenated castor oil, tristearin, tripalmitin, trimyristin, yellow wax, hard fat, fat that is useful as suppository bases, anhydrous dairy fats, lanolin, glyceryl palmitostearate, glyceryl stearate, lauryl macrogolglycerides, cetyl alcohol, polyglyceryl diisostearate, and mixtures thereof.

58. The composition of claim 53, wherein said coating comprises a single coating film comprising the composite material AB.

59. The composition of claim 29, said composition comprising a mixture of more than one population of microcapsules, each population of microcapsules containing at least one active principle, and wherein the populations differ from one another in that they have different in vitro dissolution profiles for at least one pH value of between 1.4 and 7.4.

60. The composition of claim 59, wherein at least one population of microcapsules differs from at least one other population of microcapsules through their respective triggering pHs.

61. The composition of claim 60, wherein the respective triggering pH of each of the more than one population of microcapsules is between 5 and 7.

62. The composition of claim 59, comprising at least two populations of microcapsules, and wherein at least one population of microcapsules differs from at least one other population of microcapsules through their respective triggering times.

63. The composition of claim 59, said composition comprising:

i. at least one immediate release active principle;

ii. at least one population P1 of microcapsules with modified release of the at least one active principle; and iii. at least one population P2 of microcapsules with modified release of the at least one active principle;

and wherein the respective triggering pHs of P1 and of P2 differ by at least 0.5 of a pH unit.

64. The composition of claim 59, said composition comprising:

i. at least one immediate release active principle;

ii. at least one population of microcapsules with modified release of the at least one active principle and having a triggering pH equal to 5.5; and iii. at least one population of microcapsules with modified release of the at least one active principle and having a triggering pH equal to 6.0 or 6.5.

65. The composition of claim 59, said composition having the following in vitro release profile: less than 20% of the at least one active principle is released after 2 hours at pH=1.4; and at least 50% of the at least one active principle is released after 16 hours at pH=1.4.

*66. The composition of claim 59, wherein the populations of microcapsules contain the at least one active principle in an amount that is between 5 and 80% by weight on a dry basis relative to the total mass of the microcapsules.*

*67. The composition of claim 59, wherein the populations of microcapsules contain the at least one active principle in an amount that is between 10 and 70% by weight on a dry basis relative to the total mass of the microcapsules.*

*68. The composition of claim 59, wherein the populations of microcapsules contain the at least one active principle in an amount that is between 15 and 60% by weight on a dry basis relative to the total mass of the microcapsules.*

*69. The composition of claim 29, said composition comprising at least one active principle with immediate release, the behavior of which in an in vitro dissolution test is such that at least 80% of the at least one active principle is released in 1 hour at any pH of between 1.4 and 7.4.*

*70. The composition of claim 29, wherein said composition is provided in the form of a single daily oral dose.*

*71. The composition of claim 29, comprising from 5,000 to 500,000 microcapsules with modified release of the at least one active principle.*

*72. The composition of claim 29, wherein at least one of the at least one active principle is selected from the group consisting of: antiulcer agents, antidiabetic agents, anticoagulants, antithrombics, blood lipid-lowering agents, antiarrhythmics, vasodilators, anti-angina agents, antihypertensives, vasoprotective agents, fertility promoters, inducers and inhibitors of uterine labor, contraceptives, antibiotics, antifungal agents, antiviral agents, anticancer agents, anti-inflammatories, analgesics, antiepileptics, antiparkinsonian agents, neuroleptics, hypnotics, anxiolytics, psychostimulants, antimigraine agents, antidepressants, antitussives, antihistamines or antiallergic agents, agents for combating congestive heart failure, angina pectoris, left ventricular hypertrophy, cardiac arythmias, myocardial infarctions, reflex tachycardia, ischaemic heart disease, atheromatosis, hypertension related to diabetes mellitus, portal hypertension, dizziness, bradycardia, arterial hypotension, hydrosodic retention, acute kidney failure, orthostatic hypotension, cerebral congestion, and mixtures thereof.*

*73. The composition of claim 29, wherein at least one of the at least one active principle is selected from the group of products consisting of: acetylsalicylic acid, carbamazepine, pentoxifylline, prazosine, acyclovir, nifedipine, diltiazem, naproxen, ibuprofen, flurbiprofen, ketoprofen, fenoprofen, indomethacin, diclofenac, fentiazac, oestradiol valerate, metoprolol, sulpiride, captopril, cimetidine, zidovudine, nicardipine, terfenadine, atenolol, salbutamol, carbamazepine, ranitidine, enalapril, simvastatin, fluoxetine, alprazolam, famotidine, ganciclovir, famciclovir, spironolactone, 5-asa, quinidine, perindopril, morphine, pentazocine, paracetamol, omeprazole, lansoprazole, metoclopramide, aminosalicylic acid, nalidixic acid, amoxicillin, amoxicillin and potassium clavulanate, ampicillin, ampicillin and sulbactam, azithromycin, bacampicillin, carbenicillin indanyl sodium, and other carbenicillin salts, capreomycin, cefadroxil, cefazolin, cephalexin, cephalothin, cephapirin, cephacelor, cefprozil, cephadrine, cefamandole, cefonicide, ceforanide, cefuroxime, cefixime, cefoperazone, cefotaxime, cefpodoxime, ceftaxidime, ceftibuten, ceftizoxime, ceftriaxone, cefepime, cefinetazole, cefotetan, cefoxitin, ciprofloxacine, clarithromycin, clindamycin, clofazimine, cloxacillin, cotriamoxazole, cycloserine, dicloxacillin, dirithromycin, erythromycin, erythromycin estolate, erythromycin ethylsuccinate, erythromycin gluceptate, erythromycin lactobionate, erythromycin stearate, ethambutol-HCl, other ethambutol salts, ethionamide, fosfomycin, imipenem, isoniazide, levofloxacine, lomefloxacine, loracarbef, methicillin, methenamine, metronidazole, metoclopramide, mezlocillin, nafcillin, nitrofurantoin, norfloxacin, novobiocin, ofloxacin, oxacillin, penicillin V, penicillin salts, penicillin complexes, pentamidine, piperacillin, piperacillin and tazobactam, sparfloxacin, sulphacytine, sulphamerazine, sulphamethazine, sulphamethixole, sulphasalazine, sulphisoxazole, sulphapyrizine, sulphadiazine, sulphmethoxazole, sulphapyridine, ticarcillin, ticarcillin and potassium clavulanate, trimethoprime, trimetrexate, troleanomycin, vancomycin, verapamil and mixtures thereof.*

*74. A method of therapeutic treatment, wherein the treatment comprises oral administration, according to a given dosage, of a composition of claim 29.*

* * * * *